United States Patent [19]

Bolinski et al.

[11] Patent Number: 4,744,816

[45] Date of Patent: May 17, 1988

[54] HERBICIDAL SULFONAMIDES

[75] Inventors: Martha M. Bolinski, Northeast, Md.; Donald J. Dumas, Wilmington, Del.

[73] Assignee: E. I. DuPont de Nemours and Company, Wilmington, Del.

[21] Appl. No.: 60,567

[22] Filed: Jun. 11, 1987

Related U.S. Application Data

[63] Continuation of Ser. No. 731,261, May 8, 1985, abandoned, which is a continuation-in-part of Ser. No. 618,412, Jun. 7, 1984, abandoned.

[51] Int. Cl.$^4$ .................. A01N 43/70; C07D 401/12; C07D 409/12; C07D 251/52
[52] U.S. Cl. ........................................... 71/93; 71/90; 71/91; 544/208; 544/209; 544/49
[58] Field of Search ............... 71/93, 90, 91; 544/208, 544/209, 49

[56] References Cited

U.S. PATENT DOCUMENTS 4,548,638 10/1985 Hageman et al. ................. 71/93

FOREIGN PATENT DOCUMENTS 831626 3/1983 South Africa .

Primary Examiner—John M. Ford

[57] ABSTRACT

Herbicidal sulfonamides such as 2-[[[4-(methylamino)-6-(2,2,2-trifluoroethoxy)-1,3,5-triazin-2-yl]aminocarbonyl]aminosulfonyl]benzoic acid, methyl ester are useful as herbicides and plant growth regulants.

21 Claims, No Drawings

HERBICIDAL SULFONAMIDES

RELATED APPLICATION

This application is a continuation of my copending application U.S. Ser. No. 731,261 filed May 8, 1985, now abandoned which in turn is a continuation-in-part of my copending application U.S. Ser. No. 618,412 filed June 7, 1984, now abandoned.

BACKGROUND OF THE INVENTION

The present invention relates to a class of sulfonylurea compounds which are herbicidal sulfonamides, agriculturally suitable compositions containing them and their method-of-use as preemergent and/or postemergent herbicides or plant growth regulators, as well as for agriculturally suitable salts.

U.S. Pat. No. 4,127,405 and U.S. Pat. No. 4,169,719 disclose herbicidal benzenesulfonylureas.

U.S. Pat. No. 4,394,506 and U.S. Pat. No. 4,383,113 disclose ortho-alkoxycarbonylbenzenesulfonylureas.

U.S. Pat. No. 4,370,479 discloses herbicidal naphthalene sulfonylureas.

U.S. Pat. No. 4,435,206 and EP-A-No. 35,893 disclose herbicidal pyridylsulfonylureas.

EP-A-No. 30,142 discloses thiophene sulfonylureas which are useful as herbicides.

U.S. Pat. No. 4,420,325 discloses herbicidal benzylsulfonylureas.

U.S. Ser. No. 533,341 discloses the herbicidal sulfonylureas of the following general structure:

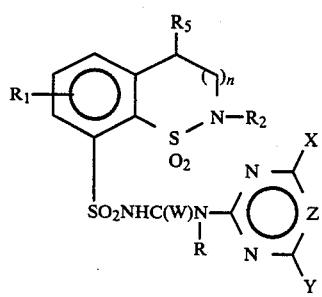

South African Patent Application No. 83/5165 filed by Ciba-Geigy (Swiss priority 7/16/82) discloses herbicidal benzo[b]furan sulfonylureas.

South African Application No. 83/8416 (Swiss priority 11/12/82; published 5/12/84) discloses sulfonylureas of the general formula

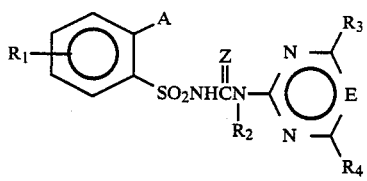

wherein
Z is O or S;
E is N or CH;
$R_1$ is, inter alia, H, halogen, $NO_2$, $C_1$–$C_4$ alkyl, etc.;
$R_3$ and $R_4$ are independently H, $C_1$–$C_4$ alkyl, $C_1$–$C_4$ haloalkoxy, $-NR_5R_6$, etc.;
$R_5$ and $R_6$ are H or $C_1$–$C_4$ alkyl; and
A is an unsaturated or partially saturated 5- or 6-membered heterocyclic ring system which is bonded through a carbon atom and contains 1, 2 or 3 heteroatoms.

South African Application No. 84/2245 (Swiss priority 3/28/83; published 9/28/84) discloses herbicidal sulfonylureas of the formula

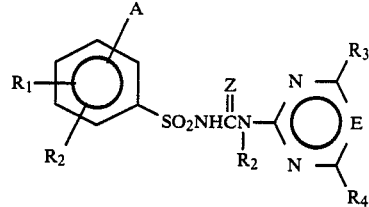

wherein
A is $C_1$–$C_6$ haloalkyl;
Z is O or S;
E is CH or N;
$R_1$ is, inter alia, H, halogen, $NO_2$, CN, etc.;
$R_2$ is, inter alia, H, halogen, $C_1$–$C_4$ alkyl, etc.;
$R_3$ and $R_4$ are independently H, halogen, $C_1$–$C_4$ alkyl, $C_2$–$C_4$ haloalkoxy, $-NR_{12}R_{13}$, etc.; and
$R_{12}$ and $R_{13}$ are independently H or $C_1$–$C_4$ alkyl, South African Application No. 84/2722 (Swiss priority 4/13/83; published 10/13/84) discloses sulfonylureas of the formula

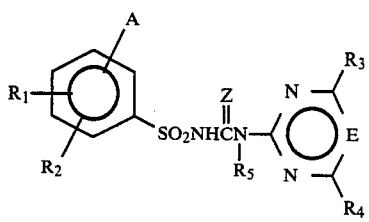

wherein
A is a radical of the formula $-CR_6R_7XR_8$, $CR_9R_{10}R_{11}$ or $CHR_7SCQR_{21}$;
$R_1$ is, inter alia, H, halogen, $NO_2$, CN, etc.;
$R_2$ is, inter alia, H, halogen, $C_1$–$C_4$ alkyl, etc.;
Z is O or S;
$R_3$ and $R_4$ are independently H, halogen, $C_1$–$C_4$ haloalkoxy, $NR_{19}R_{20}$, etc.;
$R_{19}$ and $R_{20}$ are independently H or $C_1$–$C_4$ alkyl;
$R_9$ is, inter alia, H, halogen, $C_1$–$C_4$ alkyl, etc.;
$R_{10}$ is H, halogen or $CH_3$; and
$R_{11}$ is, inter alia, a radical $C(O)R_{24}$ or a $C_1$–$C_4$ alkyl group that is mono- or poly-substituted by CN, $NO_2$, OH, $C_1$–$C_4$ alkoxy, $C_1$–$C_4$ haloalkoxy, etc.

South African Application No. 82/7439, published 4/13/83, discloses the following compounds of the formula

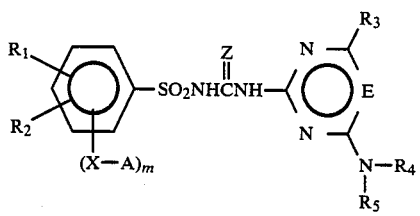

wherein
$R_4$ is H, $CH_3$ or $C_2H_5$;

$R_5$ is H, $C_1$–$C_4$ alkyl, $C_1$–$C_3$ alkoxy, $CH_2OCH_3$, $CH_2CN$ or $CH_2CH_2CN$; and $R_3$ is H, $C_1$–$C_4$ alkyl, $C_1$–$C_4$ haloalkoxy, etc.

A wide variety of materials useful for killing or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to novel compounds of Formula I, agriculturally suitable compositions containing them and their method-of-use as preemergent and postemergent herbicides or as plant growth regulants, and their agriculturally suitable salts.

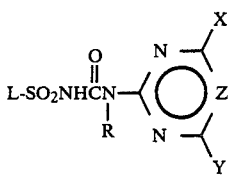

I wherein
R is H or $CH_3$;
L is

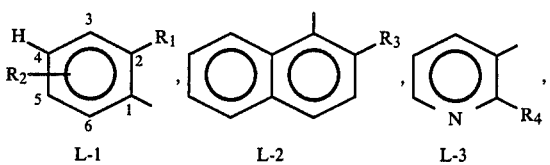

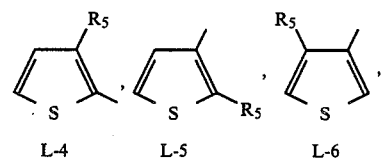

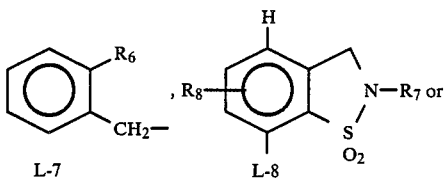

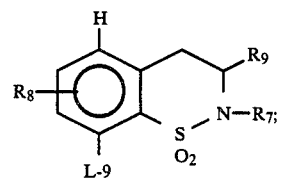

$R_1$ is $C_1$–$C_4$ alkyl, $C_1$–$C_4$ alkoxy, F, Cl, Br, $NO_2$, $CO_2R_{10}$, $SO_2NR_{11}R_{12}$, $SO_2N(OCH_3)CH_3$, $S(O)_nR_{13}$, $CH_2OCH_3$, $CH_2OC_2H_5$, $C_6H_5$ or Q;
Q is

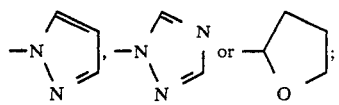

$R_2$ is H, F, Cl, Br, $CF_3$, $CH_3$, $C_2H_5$, $OCH_3$, $OC_2H_5$, $SCH_3$ or $SC_2H_5$;

$R_3$ is H, $CH_3$, $OCH_3$, F, Cl, Br, $SO_2N(CH_3)_2$, $OSO_2CH_3$ or $S(O)_nCH_3$;

$R_4$ is $CH_3$, $C_2H_5$, $OCH_3$, $OC_2H_5$, F, Cl, Br, $SO_2NR_{11}R_{12}$, $SO_2N(OCH_3)CH_3$ or $S(O)_nR_{13}$;

$R_5$ is $C_1$–$C_3$ alkyl, F, Cl, Br, $NO_2$, $CO_2R_{10}$, $SO_2NR_{11}R_{12}$, $SO_2N(OCH_3)CH_3$ or $S(O)_nR_{13}$;

$R_6$ is $CO_2CH_3$, $CO_2C_2H_5$, $SO_2N(CH_3)_2$, $OSO_2CH_3$, $SO_2CH_3$ or $SO_2CH_2CH_3$;

$R_7$ is H, $C_1$–$C_5$ alkyl, $CH_2CH_2F$, $CH_2CH_2CH_2F$, $C_3$–$C_4$ alkenyl, $C_3$–$C_4$ alkynyl, $CH_3OCH_2CH_2$ or $C_2H_5OCH_2CH_2$;

$R_8$ is H, Cl, $CH_3$ or $OCH_3$;

$R_9$ is H or $CH_3$;

$R_{10}$ is $C_1$–$C_4$ alkyl, $CH_2CH_2OCH_3$, $CH_2CH_2Cl$, $CH_2CH{=}CH_2$ or $CH_2C{\equiv}CH$;

$R_{11}$ is H or $C_1$–$C_2$ alkyl;

$R_{12}$ is $C_1$–$C_2$ alkyl;

$R_{13}$ is $C_1$–$C_3$ alkyl;

n is 0, 1 or 2;

X is $NR_{14}R_{15}$;

$R_{14}$ is H or $C_1$–$C_2$ alkyl;

$R_{15}$ is $C_1$–$C_2$ alkyl, $OCH_3$, $OC_2H_5$ or $CH_2CN$;

Y is $OCH_2CH_2F$, $OCH_2CHF_2$ or $OCH_2CF_3$; and

Z is CH or N;

and their agriculturally suitable salts.

Preferred for reasons of their higher herbicidal activity, greater plant growth regulant activity and/or more favorable ease of synthesis are:

(1) Compounds of Formula I wherein
  L is L-1, L-8 or L-9; and
  R is H.

(2) Compounds of Preferred 1 wherein
  $R_1$ is $C_1$–$C_3$ alkyl, $C_1$–$C_3$ alkoxy, Cl, $NO_2$, $CO_2C_1$–$C_3$ alkyl, $SO_2N(CH_3)_2$, $SO_2CH_3$ or $SO_2C_2H_5$;
  $R_{14}$ is H; Z is N; and
  $R_2$ is in the 5-position of the phenyl ring.

(3) Compounds of Preferred 2 wherein
  L is L-1 or L-8; and
  $R_7$ is H, $CH_3$ or $C_2H_5$.

(4) Compounds of Preferred 3 wherein
  $R_{15}$ is $CH_3$; and
  $R_2$ is H.

Specifically preferred for their greatest herbicidal activity, greatest plant growth regulant activity and/or greatest ease of synthesis:

2-[[[4-(methylamino)-6-(2,2,2-trifluoroethoxy)-1,3,5-triazin-2-yl]aminocarbonyl]aminosulfonyl]benzoic acid, methyl ester, m.p. 195°–197° C.(d); and 2-[[[4-(methylamino)-6-(2,2,2-trifluoroethoxy)-1,3,5-triazin-2-yl]aminocarbonyl]aminosulfonyl]benzoic acid, ethyl ester, m.p. 180°–183° C.(d).

DETAILED DESCRIPTION OF THE INVENTION

Synthesis

The compounds of Formula I can be prepared by reacting an appropriate sulfonyl isocyanate II with the appropriately substituted aminoheterocycle III, as shown in Equation 1. R, X, Y, Z and L are as previously defined.

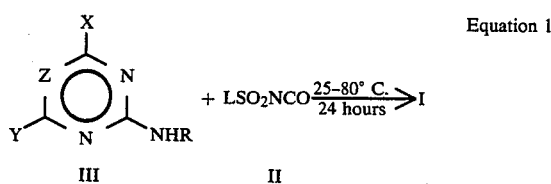

Equation 1

The reaction is best performed in an inert solvent such as methylene chloride or toluene at 25° to 100° C., for 1 to 24 hours. Isolation of the product can be achieved by concentrating the solution and trituration with an appropriate solvent such as butyl chloride.

Alternatively, compounds of Formula I may be prepared by reacting the sulfonamides of Formula IV with the carbamates of Formula V (R'=CH$_3$) in the presence of an excess of trimethylaluminum, as shown in Equation 2, where L, R, X, Y and Z are as previously defined, provided R$_1$ is other than CO$_2$R$_{10}$.

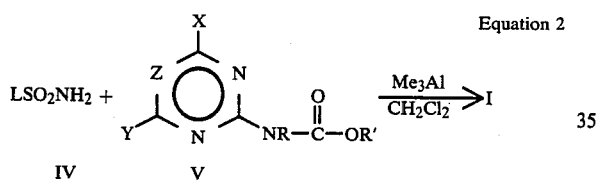

Equation 2

The reactions are best performed in an inert solvent such as methylene chloride at the reflux point of the solution (40° C.) for 10 to 24 hours. Isolation of the product is best achieved by exposing the reaction mixture to acetic acid, separation of the layers and concentrating the organic layer to a solid.

Alternatively, compounds of Formula I can be prepared by exposing a phenyl carbamate V (R'=Ph) to the sulfonamide IV in an appropriate solvent such as dioxane at 25° to 100° C. in the presence of a strong base such as 1,8-diazabicyclo[5.4.0]undec-7-ene; acid workup affords the desired product. See EPO Publication No. 44,807 for details. The required carbamates (V) can be prepared from the corresponding amines III and dimethyl or diphenyl carbonate or methyl or phenyl chloroformate and a suitable base such as sodium hydride.

The sulfonyl isocyanates II used in the preparation of I are known in the art and can be prepared by known methods. For example, isocyanates can be prepared by exposing an appropriate benzene or heterocyclic sulfonamide to phosgene in the presence of an alkyl isocyanate and an amine catalyst such as 1,4-diazabicyclo[2.2.2]octane at the reflux point of the solvent. See H. Ulrich and A. A. Y Sayigh, *Newer Methods of Preparative Organic Chemistry*, Vol. VI, p. 223–241, Academic Press, New York and London, W. Forest Ed.

The sulfonamides IV used in the preparation of I are also known in the art and can be prepared by known methods. For example, exposure of a sulfonyl chloride to ammonium hydroxide results in the formation of the corresponding sulfonamide, e.g., Crossley et al., *J. Am. Chem. Soc.*, 60, 2223 (1938). The appropriate sulfonyl chlorides are prepared by several methods. For example, treatment of a substituted aromatic or heterocyclic ring with chlorosulfonic acid in carbon tetrachloride results in the formation of the sulfonyl chloride. See Clark et al., *Org. Synth. Coll.*, Vol. 1 2nd Ed. 1941, p. 85.

An alternative method of preparation of sulfonyl chlorides can be achieved from an appropriate amine. Diazotization of an amine with sodium nitrite in acid, followed by exposure of the resulting diazonium salt to sulfur dioxide in the presence of cuprous chloride results in the formation of a sulfonyl chloride. See H. L. Yale and F. Sowinski, *J. Org. Chem.*, 25, 1824 (1960).

The heterocyclic amines III, where X, Y, Z and R are as previously defined may be prepared as outlined in Equation 3.

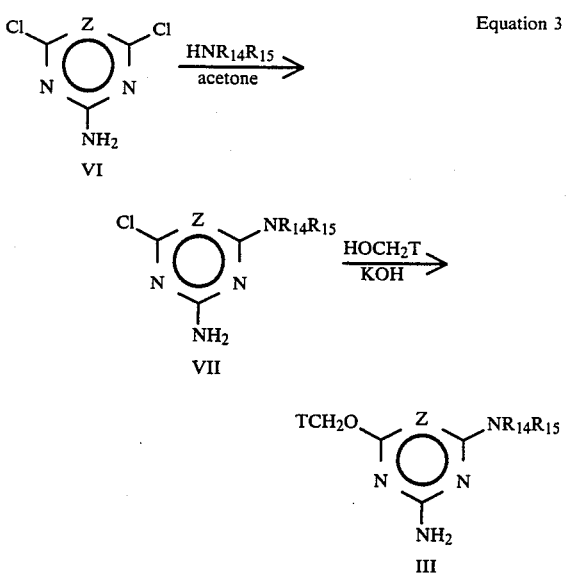

Reaction of dichloride VI with the appropriate secondary amine in acetone affords the aminated product VII. Subsequent exposure of VII with the appropriate alcohol in the presence of a suitable base such as potassium hydroxide affords the desired heterocycle III (where T is CF$_3$, CHF$_2$ or CH$_2$F).

The starting amine heterocycles VI are known in the art. For further details of their preparation see *The Chemistry of Heterocyclic Compounds*, "Interscience Publ., New York and London; P. J. Brown, "The Pyrimidines", Vol. XVI and E. M. Smolin and L. Rapoport, "s-Triazines and Derivatives", Vol. XIII.

The heterocyclic amines III where R is a methyl group may be prepared from the corresponding compounds where R is hydrogen by known methods. An example of this type of transformation is described in: *J. Chem. Soc. Perkin I*, 1569 (1981).

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The following examples teach the synthesis of some of the compounds contained within this invention in greater detail.

EXAMPLE 1

2-Amino-4-chloro-6-methylamino-1,3,5-triazine

A solution of 2-amino-4,6-dichloro-1,3,5-triazine (0.2 mole) in 200 ml reagent grade acetone was cooled to 0° C. Two equivalents of 40% aqueous methylamine were added dropwise keeping the temperature less than 10° C.; solids precipitated during the addition. The reaction was then warmed to room temperature and stirred overnight under $N_2$.

The mixture was poured onto 800 ml of ice-water and the insolubles were filtered off and washed with distilled water. The solid was dried overnight over $P_2O_5$ in a vacuum dessicator. The resulting product named above had the following characteristics: m.p. 258°-260° C. (decomp.); NMR ($CDCl_3$, DMSO-$d_6$): δ 2.8, d, (NHC$\underline{H}_3$); 6.8-7.65, mt, (N$\underline{H}_2$+N$\underline{H}$CH$_3$).

EXAMPLE 2

2-Amino-4-methylamino-6-trifluoroethoxy-1,3,5-triazine

2-Amino-4-chloro-6-methylamino-1,3,5-triazine (0.2 mole) was slurried in 80 ml of 2,2,2-trifluoroethanol at room temperature. Potassium hydroxide pellets (0.2 mole) were added portionwise and the mixture was stirred at room temperature overnight. The following day the reaction was heated at gentle reflux for 2 hours during which time the solids gradually dissolved. The solution was cooled and the solvent was removed under vacuum. The residue was washed with water and filtered to give 20.9 g shining off-white crystals of the product named above with the following characteristics: m.p. 204°-205° C. NMR (DMSO-$d_6$): δ 2.75, d, (NHC$\underline{H}_3$); 4.8, q, (OC$\underline{H}_2$CF$_3$); 6.5-7.3, m, (N$\underline{H}_2$+N$\underline{H}$CH$_3$).

EXAMPLE 3

2-[[[4-(Methylamino)-6-(2,2,2-trifluoroethoxy)-1,3,5-triazin-2-yl]aminocarbonyl]aminosulfonyl]benzoic acid, methyl ester 2-Carbomethoxybenzenesulfonyl isocyanate (0.5 g) was dissolved in 5 ml of methylene chloride. The aminoheterocycle (0.46 g) prepared in Example 2 was added and the mixture was stirred overnight under nitrogen at room temperature. The resulting solids were filtered off, washed with methylene chloride and dried to give 0.54 g of ~80% pure subject compound; m.p. 195°-197° C. decomp. No attempt was made at further purification. The resulting product named above had the following characteristics: IR (nujol) showed carbonyl bands at 1723 cm$^{-1}$ and 1740 cm$^{-1}$. NMR (CDCl$_3$, DMSO-$d_6$): δ 2.9, m, (NHC$\underline{H}_3$); 3.8, s, (CO$_2$C$\underline{H}_3$); 4.9, m, (OC$\underline{H}_2$CF$_3$); 7.7-8.4, m, (aromatic H's) plus ~20% heterocycle.

Using the procedures described above, the compounds in Tables 1-9 can be prepared by one skilled in the art.

TABLE 1a

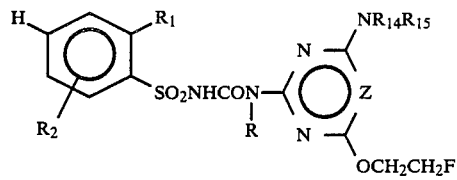

| R$_1$ | R$_2$ | R | R$_{14}$ | R$_{15}$ | Z | m.p. (°C.) |
|---|---|---|---|---|---|---|
| CH$_3$ | H | H | H | CH$_3$ | CH | |
| CH$_2$CH$_3$ | H | H | H | CH$_3$ | CH | |
| CH$_2$CH$_3$ | H | H | H | CH$_3$ | N | |
| CH$_2$CH$_2$CH$_3$ | H | H | H | CH$_3$ | N | |
| CH$_2$CH$_2$CH$_3$ | H | H | CH$_3$ | CH$_3$ | N | |
| OCH$_3$ | H | H | H | CH$_3$ | N | |
| OCH$_3$ | H | H | CH$_2$CH$_3$ | CH$_3$ | CH | |
| OCH$_2$CH$_3$ | H | H | H | CH$_3$ | N | |
| OCH$_2$CH$_3$ | H | H | CH$_3$ | CH$_3$ | N | |
| OCH$_2$CH$_3$ | H | H | H | CH$_2$CH$_3$ | CH | |
| OCH$_2$CH$_2$CH$_3$ | H | H | H | CH$_3$ | N | |
| OCH$_2$CH$_2$CH$_3$ | H | H | H | CH$_3$ | CH | |
| OCH$_2$CH$_2$CH$_3$ | H | H | H | CH$_2$CH$_3$ | N | |
| OCH$_2$CH$_2$CH$_2$CH$_3$ | H | H | H | CH$_3$ | N | |
| F | H | H | H | CH$_3$ | CH | |
| F | H | H | H | CH$_3$ | N | |
| F | H | H | CH$_3$ | CH$_3$ | N | |
| F | H | H | H | CH$_2$CH$_3$ | N | |
| F | H | H | H | CH$_2$CH$_3$ | CH | |

TABLE 1a-continued

[Structure: phenyl ring with H (para), R₁ (ortho), R₂ (meta), SO₂NHCON(R)- connected to a pyrimidine/triazine bearing NR₁₄R₁₅ and OCH₂CH₂F substituents with Z in ring]

| R₁ | R₂ | R | R₁₄ | R₁₅ | Z | m.p. (°C) |
|---|---|---|---|---|---|---|
| F | H | H | $CH_2CH_3$ | $CH_2CH_3$ | N | |
| Cl | H | H | H | $CH_3$ | N | |
| Cl | H | H | H | $CH_3$ | CH | |
| Cl | H | H | $CH_3$ | $CH_3$ | N | |
| Cl | H | H | $CH_3$ | $CH_3$ | CH | |
| Cl | H | H | $CH_3$ | $CH_2CH_3$ | N | |
| Q-1 | H | H | $CH_3$ | $CH_3$ | N | |
| Q-1 | H | H | $CH_3$ | $CH_3$ | CH | |
| Br | H | H | H | $CH_3$ | N | |
| Br | H | H | H | $CH_3$ | CH | |
| Br | H | H | $CH_3$ | $CH_3$ | N | |
| Br | H | H | $CH_3$ | $CH_3$ | CH | |
| Br | 6-$OCH_3$ | H | H | $CH_3$ | N | |
| $NO_2$ | H | H | H | $CH_3$ | N | |
| $NO_2$ | H | H | H | $CH_3$ | CH | |
| $NO_2$ | H | H | $CH_3$ | $CH_3$ | N | |
| $NO_2$ | H | $CH_3$ | $CH_3$ | $CH_3$ | N | |
| $NO_2$ | F | H | H | $CH_3$ | N | |
| $CO_2CH_3$ | H | H | H | $CH_3$ | N | |
| $CO_2CH_3$ | H | H | H | $CH_3$ | CH | |
| $CO_2CH_3$ | H | H | H | $CH_2CH_3$ | CH | |
| $CO_2CH_3$ | H | H | H | $CH_2CH_3$ | N | |
| $CO_2CH_3$ | H | H | $CH_3$ | $CH_3$ | N | |
| $CO_2CH_3$ | H | H | $CH_3$ | $CH_3$ | CH | |
| $CO_2CH_3$ | H | H | $CH_3$ | $CH_2CH_3$ | CH | |
| $CO_2CH_3$ | H | H | $CH_3$ | $CH_2CH_3$ | N | |
| $CO_2CH_3$ | H | H | $CH_2CH_3$ | $CH_2CH_3$ | N | |
| $CO_2CH_3$ | H | H | $CH_2CH_3$ | $CH_2CH_3$ | CH | |
| $SO_2N(CH_3)_2$ | H | H | H | $CH_3$ | CH | |
| $SO_2N(CH_3)_2$ | H | H | H | $CH_3$ | N | |
| $SO_2N(CH_3)_2$ | H | H | $CH_3$ | $CH_3$ | CH | |
| $SO_2N(CH_3)_2$ | H | H | $CH_3$ | $CH_3$ | N | |
| $SO_2N(CH_3)_2$ | H | H | $CH_3$ | $CH_2CH_3$ | CH | |
| $SO_2N(CH_2CH_3)CH_3$ | H | H | H | $CH_3$ | N | |
| $SO_2N(CH_2CH_3)CH_3$ | H | H | H | $CH_3$ | CH | |
| $SO_2N(CH_2CH_3)CH_3$ | H | H | $CH_3$ | $CH_3$ | N | |
| $SO_2N(CH_2CH_3)_2$ | H | H | H | $CH_3$ | N | |
| $SO_2N(CH_2CH_3)_2$ | H | H | H | $CH_3$ | CH | |
| $SO_2N(OCH_3)CH_3$ | H | H | H | $CH_3$ | N | |
| $SO_2N(OCH_3)CH_3$ | H | H | H | $CH_3$ | CH | |
| $SO_2N(OCH_3)CH_3$ | H | H | H | $CH_2CH_3$ | N | |
| $SO_2N(OCH_3)CH_3$ | H | H | $CH_3$ | $CH_3$ | N | |
| $SO_2CH_3$ | H | H | H | $CH_3$ | N | |
| $SO_2CH_3$ | H | H | H | $CH_3$ | CH | |
| $SO_2CH_2CH_3$ | H | H | H | $CH_3$ | N | |
| $SO_2CH_2CH_2CH_3$ | H | H | H | $CH_3$ | N | |
| $SO_2CH_2CH_2CH_3$ | H | $CH_3$ | H | $CH_3$ | N | |
| $SCH_2CH_2CH_3$ | 5-$OCH_3$ | H | H | $CH_3$ | N | |
| Ph | H | H | $CH_3$ | $CH_3$ | N | |
| Ph | H | H | H | $CH_3$ | N | |
| $CH_3$ | H | H | H | $CH_2CN$ | N | |
| $CH_3$ | H | H | H | $OCH_3$ | CH | |
| $CH_2CH_3$ | H | H | H | $OCH_3$ | N | |
| $CH_2CH_2CH_2CH_3$ | H | H | H | $OCH_3$ | N | |
| $OCH_3$ | 5-$SCH_3$ | H | H | $CH_3$ | CH | |
| $OCH_2CH_3$ | 5-$SCH_3$ | H | H | $CH_3$ | N | |
| F | H | H | H | $OCH_3$ | N | |
| F | H | H | $CH_3$ | $OCH_3$ | N | |
| Cl | H | H | H | $OCH_3$ | CH | |
| Cl | 5-$SCH_3$ | H | H | $CH_3$ | N | |
| Br | 5-$SCH_3$ | H | H | $CH_3$ | CH | |
| Br | H | H | $CH_3$ | $OCH_3$ | N | |
| $CO_2CH_3$ | H | H | $CH_3$ | $OCH_3$ | N | |
| $CO_2CH_3$ | H | H | $CH_3$ | $OCH_3$ | CH | |
| $CO_2CH_3$ | 5-$SCH_3$ | H | H | $CH_3$ | N | |
| $CO_2CH_3$ | H | H | H | $OCH_3$ | N | |
| $SO_2N(CH_3)_2$ | H | H | $CH_3$ | $OCH_3$ | N | |
| $SO_2N(CH_3)_2$ | H | H | $CH_3$ | $CH_2CN$ | N | |
| $SO_2N(CH_3)H$ | H | H | H | $CH_3$ | CH | |
| Q-1 | H | H | H | $CH_3$ | CH | |
| Q-1 | H | H | H | $CH_3$ | N | |

TABLE 1a-continued

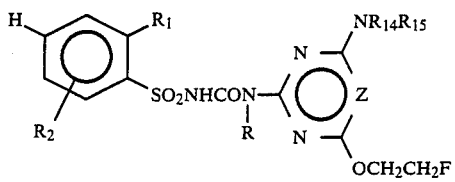

| R₁ | R₂ | R | R₁₄ | R₁₅ | Z | m.p. (°C.) |
|---|---|---|---|---|---|---|
| Q-2 | H | H | H | CH₃ | N | |
| Q-2 | H | H | CH₃ | OCH₃ | N | |
| Q-3 | H | H | H | CH₃ | N | |
| CH₃ | H | H | CH₃ | OCH₃ | CH | |
| CH₃ | H | H | CH₃ | OCH₃ | N | |
| CH₂CH₃ | H | H | CH₃ | OCH₃ | N | |
| Cl | H | H | CH₃ | OCH₃ | N | |
| NO₂ | H | H | CH₃ | OCH₃ | N | |
| CO₂CH₃ | 5-OCH₃ | H | CH₃ | OCH₃ | CH | |
| CO₂CH₃ | 5-CF₃ | H | CH₃ | OCH₃ | CH | |
| CO₂CH₃ | H | CH₃ | CH₃ | OCH₃ | N | |
| CO₂CH₂CH₃ | H | H | CH₃ | OCH₃ | N | |
| CO₂CH₂CH=CH₂ | H | H | CH₃ | OCH₃ | N | |
| SO₂N(CH₃)₂ | H | H | CH₃ | OCH₃ | CH | |
| CH₂OCH₃ | H | H | CH₃ | OCH₃ | N | |

TABLE 1b

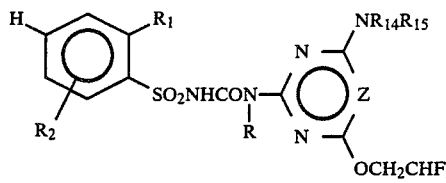

| R₁ | R₂ | R | R₁₄ | R₁₅ | Z | m.p. (°C.) |
|---|---|---|---|---|---|---|
| CH₃ | H | H | H | CH₃ | CH | |
| CH₂CH₃ | H | H | H | CH₃ | CH | |
| CH₂CH₃ | H | H | H | CH₃ | N | |
| CH₂CH₂CH₃ | H | H | H | CH₃ | N | |
| CH₂CH₂CH₃ | H | H | CH₃ | CH₃ | N | |
| OCH₃ | H | H | H | CH₃ | N | |
| OCH₃ | H | H | CH₂CH₃ | CH₃ | CH | |
| OCH₂CH₃ | H | H | H | CH₃ | N | |
| OCH₂CH₃ | H | H | CH₃ | CH₃ | N | |
| OCH₂CH₃ | H | H | H | CH₂CH₃ | CH | |
| OCH₂CH₂CH₃ | H | H | H | CH₃ | N | |
| OCH₂CH₂CH₃ | H | H | H | CH₃ | CH | |
| OCH₂CH₂CH₃ | H | H | H | CH₂CH₃ | N | |
| OCH₂CH₂CH₂CH₃ | H | H | H | CH₃ | N | |
| F | H | H | H | CH₃ | CH | |
| F | H | H | H | CH₃ | N | |
| F | H | H | CH₃ | CH₃ | N | |
| F | H | H | H | CH₂CH₃ | N | |
| F | H | H | H | CH₂CH₃ | CH | |
| F | H | H | CH₂CH₃ | CH₂CH₃ | N | |
| Cl | H | H | H | CH₃ | N | |
| Cl | H | H | H | CH₃ | CH | |
| Cl | H | H | CH₃ | CH₃ | N | |
| Cl | H | H | CH₃ | CH₃ | CH | |
| Cl | H | H | CH₃ | CH₂CH₃ | N | |
| Br | H | H | H | CH₃ | N | |
| Br | H | H | H | CH₃ | CH | |
| Br | H | H | CH₃ | CH₃ | N | |
| Br | H | H | CH₃ | CH₃ | CH | |
| Br | 6-OCH₃ | H | H | CH₃ | N | |
| NO₂ | H | H | H | CH₃ | N | |
| NO₂ | H | H | H | CH₃ | CH | |
| NO₂ | H | H | CH₃ | CH₃ | N | |
| NO₂ | H | CH₃ | CH₃ | CH₃ | N | |
| NO₂ | F | H | H | CH₃ | N | |
| CO₂CH₃ | H | H | H | CH₃ | N | |
| CO₂CH₃ | H | H | H | CH₃ | CH | |
| CO₂CH₃ | H | H | H | CH₂CH₃ | CH | |
| CO₂CH₃ | H | H | H | CH₂CH₃ | N | |
| CO₂CH₃ | H | H | CH₃ | CH₃ | N | |
| CO₂CH₃ | H | H | CH₃ | CH₃ | CH | |

TABLE 1b-continued

Structure: phenyl ring with H (para), R₁ (ortho), R₂ (meta), SO₂NHCON(R)— linked to pyrimidine bearing NR₁₄R₁₅, Z, and OCH₂CHF₂ substituents.

| R₁ | R₂ | R | R₁₄ | R₁₅ | Z | m.p. (°C.) |
|---|---|---|---|---|---|---|
| CO₂CH₃ | H | H | CH₃ | CH₂CH₃ | CH | |
| CO₂CH₃ | H | H | CH₃ | CH₂CH₃ | N | |
| CO₂CH₃ | H | H | CH₂CH₃ | CH₂CH₃ | N | |
| CO₂CH₃ | H | H | CH₂CH₃ | CH₂CH₃ | CH | |
| SO₂N(CH₃)₂ | H | H | H | CH₃ | CH | |
| SO₂N(CH₃)₂ | H | H | H | CH₃ | N | |
| SO₂N(CH₃)₂ | H | H | CH₃ | CH₃ | CH | |
| SO₂N(CH₃)₂ | H | H | CH₃ | CH₃ | N | |
| SO₂N(CH₃)₂ | H | H | CH₃ | CH₂CH₃ | CH | |
| SO₂N(CH₂CH₃)CH₃ | H | H | H | CH₃ | N | |
| SO₂N(CH₂CH₃)CH₃ | H | H | H | CH₃ | CH | |
| SO₂N(CH₂CH₃)CH₃ | H | H | CH₃ | CH₃ | N | |
| SO₂N(CH₂CH₃)₂ | H | H | H | CH₃ | N | |
| SO₂N(CH₂CH₃)₂ | H | H | H | CH₃ | CH | |
| SO₂N(OCH₃)CH₃ | H | H | H | CH₃ | N | |
| SO₂N(OCH₃)CH₃ | H | H | H | CH₃ | CH | |
| SO₂N(OCH₃)CH₃ | H | H | H | CH₂CH₃ | N | |
| SO₂N(OCH₃)CH₃ | H | H | CH₃ | CH₃ | N | |
| SO₂CH₃ | H | H | H | CH₃ | N | |
| SO₂CH₃ | H | H | H | CH₃ | CH | |
| SO₂CH₂CH₂CH₃ | H | H | H | CH₃ | N | |
| SO₂CH₂CH₂CH₃ | H | H | H | CH₃ | N | |
| SO₂CH₂CH₂CH₃ | H | CH₃ | H | CH₃ | N | |
| SCH₂CH₂CH₃ | 6-OCH₃ | H | H | CH₃ | N | |
| Ph | H | H | H | CH₃ | CH | |
| Q-3 | H | H | H | CH₂CH₃ | N | |
| CH₃ | H | H | H | OCH₃ | N | |
| CH₃ | H | H | H | CH₂CN | N | |
| CH₂CH₃ | H | H | H | OCH₃ | N | |
| CH₂CH₂CH₂CH₃ | H | H | CH₃ | CH₃ | N | |
| CH₂CH₂CH₂CH₃ | H | H | H | OCH₃ | N | |
| OCH₃ | 5-SCH₃ | H | H | CH₃ | N | |
| F | H | H | CH₃ | OCH₃ | N | |
| F | H | H | CH₃ | OCH₂CH₃ | N | |
| Cl | H | H | H | OCH₃ | CH | |
| Cl | 5-SCH₃ | H | H | CH₃ | N | |
| Br | 5-SCH₃ | H | H | CH₃ | CH | |
| Br | H | H | CH₃ | OCH₃ | N | |
| CO₂CH₃ | H | H | CH₃ | OCH₃ | CH | |
| CO₂CH₃ | 5-SCH₃ | H | H | CH₃ | CH | |
| CO₂CH₃ | H | H | H | OCH₃ | N | |
| SO₂N(CH₃)₂ | 5-SCH₃ | H | H | CH₃ | N | |
| SO₂N(CH₃)₂ | H | H | CH₃ | CH₂CN | N | |
| SO₂N(CH₃)H | H | H | H | CH₃ | N | |
| Q-1 | H | H | H | CH₃ | CH | |
| Q-1 | H | H | H | CH₃ | N | |
| Q-2 | H | H | H | CH₃ | N | |
| Q-2 | H | H | CH₃ | OCH₃ | N | |
| Q-3 | H | H | H | CH₃ | N | |
| CH₃ | H | H | CH₃ | OCH₃ | N | |
| CH₂CH₃ | H | H | CH₃ | OCH₃ | N | |
| Cl | H | H | CH₃ | OCH₃ | N | |
| NO₂ | H | H | CH₃ | OCH₃ | N | |
| CO₂CH₃ | 5-OCH₃ | H | CH₃ | OCH₃ | CH | |
| CO₂CH₃ | H | CH₃ | CH₃ | OCH₃ | N | |
| CO₂CH₂CH₃ | H | H | CH₃ | OCH₃ | N | |
| CO₂CH₂CH=CH₂ | H | H | CH₃ | OCH₃ | N | |
| SO₂N(CH₃)₂ | H | H | CH₃ | OCH₃ | CH | |
| CH₂OCH₃ | H | H | CH₃ | OCH₃ | N | |

TABLE 1c

[Structure: phenyl ring with H (para), $R_1$ (ortho), $R_2$ (meta), $SO_2NHCON(R)$— linked to pyrimidine/triazine ring with $NR_{14}R_{15}$, $Z$, and $OCH_2CF_3$ substituents]

| $R_1$ | $R_2$ | R | $R_{14}$ | $R_{15}$ | Z | m.p. (°C.) |
|---|---|---|---|---|---|---|
| CH₃ | H | H | H | CH₃ | CH | |
| CH₂CH₃ | H | H | H | CH₃ | CH | |
| CH₂CH₃ | H | H | H | CH₃ | N | |
| CH₂CH₂CH₃ | H | H | H | CH₃ | N | |
| CH₂CH₂CH₃ | H | H | CH₃ | CH₃ | N | |
| OCH₃ | H | H | H | CH₃ | N | 204–207(d) |
| OCH₃ | H | H | CH₂CH₃ | CH₃ | CH | |
| OCH₂CH₃ | H | H | H | CH₃ | N | |
| OCH₂CH₃ | H | H | CH₃ | CH₃ | N | |
| OCH₂CH₃ | H | H | H | CH₂CH₃ | CH | |
| OCH₂CH₂CH₃ | H | H | H | CH₃ | N | |
| OCH₂CH₂CH₃ | H | H | H | CH₃ | CH | |
| OCH₂CH₂CH₃ | H | H | H | CH₂CH₃ | N | |
| OCH₂CH₂CH₂CH₃ | H | H | H | CH₃ | N | |
| CO₂CH₂CH₃ | H | H | H | CH₃ | N | 181–183(d) |
| CF₃ | H | H | H | CH₃ | N | 210–211(d) |
| F | H | H | CH₃ | CH₃ | N | |
| F | H | H | H | CH₂CH₃ | N | |
| F | H | H | H | CH₂CH₃ | CH | |
| F | H | H | CH₂CH₃ | CH₂CH₃ | N | |
| Cl | H | H | H | CH₃ | N | 210–212(d) |
| Cl | H | H | H | CH₃ | CH | |
| Cl | H | H | CH₃ | CH₃ | N | |
| Cl | H | H | CH₃ | CH₃ | CH | |
| Cl | H | H | CH₃ | CH₂CH₃ | N | |
| Br | H | H | H | CH₃ | N | |
| Br | H | H | H | CH₃ | CH | |
| Br | H | H | CH₃ | CH₃ | N | |
| Br | H | H | CH₃ | CH₃ | CH | |
| Br | 6-OCH₃ | H | H | CH₃ | N | |
| NO₂ | H | H | H | CH₃ | N | |
| NO₂ | H | H | H | CH₃ | CH | 207–213(d) |
| NO₂ | H | H | CH₃ | CH₃ | N | |
| NO₂ | H | CH₃ | CH₃ | CH₃ | N | |
| NO₂ | F | H | H | CH₃ | N | |
| CO₂CH₃ | H | H | H | CH₃ | N | 195–197(d) |
| CO₂CH₃ | H | H | H | CH₃ | CH | |
| CO₂CH₃ | H | H | H | CH₂CH₃ | CH | |
| CO₂CH₃ | H | H | H | CH₂CH₃ | N | 193–194(d) |
| CO₂CH₃ | H | H | CH₃ | CH₃ | N | |
| CO₂CH₃ | H | H | CH₃ | CH₃ | CH | |
| CO₂CH₃ | H | H | CH₃ | CH₂CH₃ | CH | |
| CO₂CH₃ | H | H | CH₃ | CH₂CH₃ | N | |
| CO₂CH₃ | H | H | CH₂CH₃ | CH₂CH₃ | N | |
| CO₂CH₃ | H | H | CH₂CH₃ | CH₂CH₃ | CH | |
| SO₂N(CH₃)₂ | H | H | H | CH₃ | CH | |
| SO₂N(CH₃)₂ | H | H | H | CH₃ | N | 190–205 |
| SO₂N(CH₃)₂ | H | H | CH₃ | CH₃ | CH | |
| SO₂N(CH₃)₂ | H | H | CH₃ | CH₃ | N | |
| SO₂N(CH₃)₂ | H | H | CH₃ | CH₂CH₃ | CH | |
| SO₂N(CH₂CH₃)CH₃ | H | H | H | CH₃ | N | |
| SO₂N(CH₂CH₃)CH₃ | H | H | H | CH₃ | CH | |
| SO₂N(CH₂CH₃)CH₃ | H | H | CH₃ | CH₃ | N | |
| SO₂N(CH₂CH₃)₂ | H | H | H | CH₃ | N | |
| SCH₃ | H | H | H | CH₃ | N | 200–201(d) |
| SO₂N(OCH₃)CH₃ | H | H | H | CH₃ | N | |
| SO₂N(OCH₃)CH₃ | H | H | H | CH₃ | CH | |
| SO₂N(OCH₃)CH₃ | H | H | H | CH₂CH₃ | N | |
| SO₂N(OCH₃)CH₃ | H | H | CH₃ | CH₃ | N | |
| SO₂CH₂CH₂CH₃ | 5-OCH₃ | H | H | CH₃ | N | |
| SO₂CH₃ | H | H | H | CH₃ | N | 164–165(d) |
| SOCH₃ | H | H | H | CH₃ | N | |
| SOCH₂CH₃ | H | H | H | CH₃ | CH | |
| CH₃ | H | H | H | OCH₃ | N | |
| CH₃ | H | H | H | CH₂CN | N | |
| CH₂CH₃ | H | H | H | OCH₃ | N | |
| CH₂CH₃ | H | H | H | OCH₂CH₃ | N | |
| CH₂CH₂CH₂CH₃ | H | H | H | OCH₃ | N | |
| OCH₃ | 5-SCH₃ | H | H | CH₃ | CH | |
| OCH₂CH₂CH₃ | 5-SCH₃ | H | H | CH₃ | N | |
| F | H | H | H | OCH₃ | N | |

TABLE 1c-continued

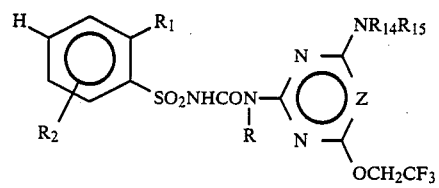

| R₁ | R₂ | R | R₁₄ | R₁₅ | Z | m.p. (°C.) |
|---|---|---|---|---|---|---|
| F | H | H | CH₃ | OCH₂CH₃ | N | |
| Cl | H | H | H | OCH₃ | CH | |
| Cl | H | H | CH₃ | CH₂CN | N | 90–100 |
| Cl | 5-SCH₃ | H | H | CH₃ | N | |
| Br | 5-SCH₃ | H | H | CH₃ | CH | |
| Br | H | H | CH₃ | OCH₃ | N | |
| CO₂CH₃ | H | H | CH₃ | OCH₃ | N | |
| CO₂CH₃ | H | H | CH₃ | OCH₃ | CH | |
| CO₂CH₃ | H | H | CH₃ | CH₂CN | N | 181–183 |
| CO₂CH₃ | 5-SCH₃ | H | H | CH₃ | N | |
| CO₂CH₃ | H | H | H | OCH₃ | N | |
| SO₂N(CH₃)₂ | H | H | CH₃ | OCH₃ | N | |
| SO₂N(CH₃)₂ | H | H | CH₃ | CH₂CN | N | |
| SO₂N(CH₃)H | H | H | H | CH₃ | N | |
| Q-1 | H | H | H | CH₃ | CH | |
| Q-1 | 5-SCH₃ | H | H | CH₃ | N | |
| Q-2 | H | H | H | CH₃ | N | |
| Q-2 | 5-SCH₃ | H | H | CH₃ | N | |
| Q-3 | H | H | H | CH₃ | N | |
| CH₃ | H | H | CH₃ | OCH₃ | N | |
| CH₂CH₃ | H | H | CH₃ | OCH₃ | N | |
| Cl | H | H | CH₃ | OCH₃ | N | |
| NO₂ | H | H | CH₃ | OCH₃ | N | |
| CO₂CH₃ | 5-OCH₃ | H | CH₃ | OCH₃ | CH | |
| CO₂CH₃ | H | CH₃ | CH₃ | OCH₃ | N | |
| CO₂CH₂CH₃ | H | H | CH₃ | OCH₃ | N | |
| SO₂N(CH₃)₂ | H | H | CH₃ | OCH₃ | CH | |
| CH₂OCH₃ | H | H | CH₃ | OCH₃ | N | |

TABLE 2a

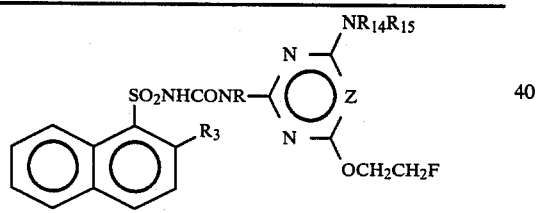

| R | R₃ | R₁₄ | R₁₅ | Z | m.p. (°C.) |
|---|---|---|---|---|---|
| H | H | H | CH₃ | N | |
| H | CH₃ | H | CH₃ | N | |
| H | CH₃ | H | CH₃ | CH | |
| H | CH₃ | CH₃ | CH₃ | N | |
| H | OCH₃ | H | CH₃ | CH | |
| H | OCH₃ | CH₃ | CH₃ | N | |
| H | F | H | CH₃ | N | |
| H | Cl | H | CH₃ | CH | |
| H | Br | H | CH₃ | N | |
| H | SO₂N(CH₃)₂ | H | CH₃ | CH | |
| H | SO₂N(CH₃)₂ | H | CH₃ | N | |
| H | SO₂N(CH₃)₂ | CH₃ | CH₂CH₃ | CH | |
| H | OSO₂CH₃ | H | CH₃ | CH | |
| H | OSO₂CH₃ | H | CH₃ | N | |
| H | OSO₂CH₃ | H | CH₂CH₃ | CH | |
| H | OSO₂CH₃ | CH₂CH₃ | CH₂CH₃ | N | |
| H | SO₂CH₃ | H | CH₃ | CH | |
| H | SO₂CH₃ | H | CH₃ | N | |
| H | SO₂CH₃ | H | CH₂CH₃ | N | |
| H | SO₂CH₃ | CH₃ | CH₃ | CH | |
| H | SO₂CH₃ | CH₃ | CH₃ | N | |
| CH₃ | SO₂CH₃ | CH₃ | CH₃ | N | |
| CH₃ | SO₂CH₃ | H | CH₃ | N | |
| H | SCH₃ | H | CH₃ | N | |
| H | SOCH₃ | H | CH₃ | N | |
| H | H | CH₃ | OCH₃ | N | |
| H | CH₃ | CH₃ | OCH₃ | CH | |

TABLE 2a-continued

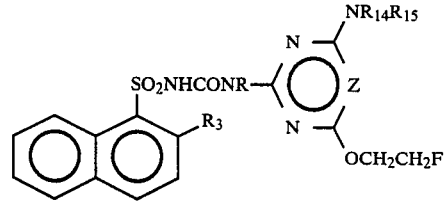

| R | R₃ | R₁₄ | R₁₅ | Z | m.p. (°C.) |
|---|---|---|---|---|---|
| H | OCH₃ | CH₃ | OCH₃ | N | |
| H | F | CH₃ | OCH₃ | CH | |
| H | F | CH₃ | OCH₃ | N | |
| H | Br | CH₃ | OCH₃ | CH | |
| H | SO₂N(CH₃)₂ | CH₃ | OCH₃ | CH | |
| H | SO₂N(CH₃)₂ | CH₃ | OCH₃ | N | |
| H | OSO₂CH₃ | CH₃ | OCH₃ | CH | |
| H | SO₂CH₃ | CH₃ | OCH₃ | N | |
| CH₃ | SO₂N(CH₃)₂ | CH₃ | OCH₃ | CH | |
| H | SO₂N(CH₃)₂ | CH₃ | OCH₂CH₃ | N | |
| H | SO₂N(CH₃)₂ | H | CH₂CN | N | |
| H | CH₃ | CH₃ | CH₂CN | N | |
| H | Cl | CH₃ | OCH₂CH₃ | N | |

TABLE 2b

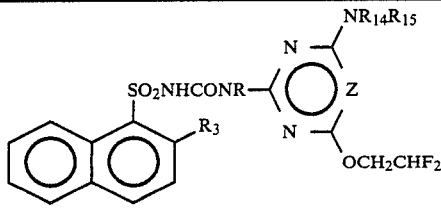

| R | R3 | R14 | R15 | Z | m.p. (°C.) |
|---|---|---|---|---|---|
| H | H | H | CH3 | N | |
| H | CH3 | H | CH3 | N | |
| H | CH3 | H | CH3 | CH | |
| H | CH3 | CH3 | CH3 | N | |
| H | OCH3 | H | CH3 | CH | |
| H | OCH3 | CH3 | CH3 | N | |
| H | F | H | CH3 | N | |
| H | Cl | H | CH3 | CH | |
| H | Br | H | CH3 | N | |
| H | SO2N(CH3)2 | H | CH3 | CH | |
| H | SO2N(CH3)2 | H | CH3 | N | |
| H | SO2N(CH3)2 | CH3 | CH2CH3 | CH | |
| H | OSO2CH3 | H | CH3 | CH | |
| H | OSO2CH3 | H | CH3 | N | |
| H | OSO2CH3 | H | CH2CH3 | CH | |
| H | OSO2CH3 | CH2CH3 | CH2CH3 | N | |
| H | SO2CH3 | H | CH3 | CH | |
| H | SO2CH3 | H | CH3 | N | |
| H | SO2CH3 | H | CH2CH3 | N | |
| H | SO2CH3 | CH3 | CH3 | CH | |
| H | SO2CH3 | CH3 | CH3 | N | |
| CH3 | SO2CH3 | CH3 | CH3 | N | |
| CH3 | SO2CH3 | H | CH3 | N | |
| H | SCH3 | H | CH3 | N | |
| H | H | CH3 | OCH3 | N | |
| H | CH3 | CH3 | OCH3 | N | |
| H | OCH3 | CH3 | OCH3 | N | |
| H | OCH3 | CH3 | OCH3 | CH | |
| H | F | CH3 | OCH3 | N | |
| H | Br | CH3 | OCH3 | CH | |
| H | SO2N(CH3)2 | CH3 | OCH3 | CH | |
| H | OSO2CH3 | CH3 | OCH3 | N | |
| H | OSO2CH3 | CH3 | OCH3 | CH | |
| H | SO2CH3 | CH3 | OCH3 | CH | |
| CH3 | SO2N(CH3)2 | CH3 | OCH3 | N | |
| H | SO2N(CH3)2 | H | CH2CN | N | |
| H | CH3 | CH3 | OCH2CH3 | N | |
| H | Cl | CH3 | OCH2CH3 | N | |

TABLE 2c

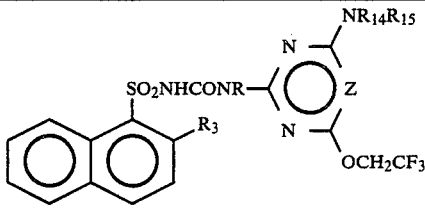

| R | R3 | R14 | R15 | Z | m.p. (°C.) |
|---|---|---|---|---|---|
| H | H | H | CH3 | N | |
| H | CH3 | H | CH3 | N | |
| H | CH3 | H | CH3 | CH | |
| H | CH3 | CH3 | CH3 | N | |
| H | OCH3 | H | CH3 | CH | |
| H | OCH3 | CH3 | CH3 | N | |
| H | F | H | CH3 | N | |
| H | Cl | H | CH3 | CH | |
| H | Br | H | CH3 | N | |
| H | SO2N(CH3)2 | H | CH3 | CH | |
| H | SO2N(CH3)2 | H | CH3 | N | |
| H | SO2N(CH3)2 | CH3 | CH2CH3 | CH | |
| H | OSO2CH3 | H | CH3 | CH | |
| H | OSO2CH3 | H | CH3 | N | |
| H | OSO2CH3 | H | CH2CH3 | CH | |
| H | OSO2CH3 | CH2CH3 | CH2CH3 | N | |

TABLE 2c-continued

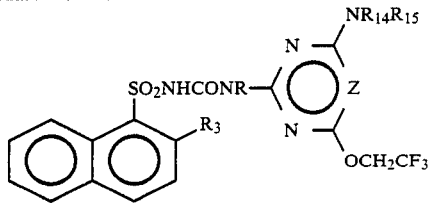

| R | R3 | R14 | R15 | Z | m.p. (°C.) |
|---|---|---|---|---|---|
| H | SO2CH3 | H | CH3 | CH | |
| H | SO2CH3 | H | CH3 | N | |
| H | SO2CH3 | H | CH2CH3 | N | |
| H | SO2CH3 | CH3 | CH3 | CH | |
| H | SO2CH3 | CH3 | CH3 | N | |
| CH3 | SO2CH3 | CH3 | CH3 | N | |
| CH3 | SO2CH3 | H | CH3 | N | |
| H | H | CH3 | OCH3 | N | |
| H | CH3 | CH3 | OCH3 | CH | |
| H | CH3 | CH3 | OCH3 | N | |
| H | OCH3 | CH3 | OCH3 | CH | |
| H | F | CH3 | OCH3 | CH | |
| H | Br | CH3 | OCH3 | CH | |
| H | Br | CH3 | OCH3 | N | |
| H | SO2N(CH3)2 | CH3 | OCH3 | CH | |
| H | OSO2CH3 | CH3 | OCH3 | N | |
| H | SO2CH3 | CH3 | OCH3 | CH | |
| H | SO2N(CH3)2 | H | CH2CN | N | |
| H | CH3 | CH3 | OCH2CH3 | N | |
| H | Cl | CH3 | OCH2CH3 | N | |

TABLE 3a

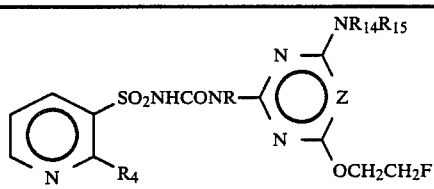

| R | R4 | R14 | R15 | Z | m.p. (°C.) |
|---|---|---|---|---|---|
| CH3 | CH3 | H | CH3 | N | |
| H | CH3 | H | CH3 | N | |
| H | CH3 | H | CH3 | CH | |
| H | CH2CH3 | H | CH3 | N | |
| H | CH2CH3 | H | CH2CH3 | CH | |
| H | OCH3 | H | CH3 | CH | |
| H | OCH3 | H | CH3 | N | |
| H | OCH3 | CH3 | CH3 | N | |
| H | OCH2CH3 | H | CH3 | N | |
| H | F | H | CH3 | N | |
| H | Cl | H | CH3 | CH | |
| H | Br | H | CH3 | CH | |
| H | Br | CH3 | CH3 | N | |
| H | SO2N(CH3)2 | H | CH3 | CH | |
| H | SO2N(CH3)2 | H | CH3 | N | |
| H | SO2N(CH3)2 | CH3 | CH3 | CH | |
| H | SO2N(CH3)2 | CH3 | CH2CH3 | N | |
| H | SO2N(CH3)2 | CH2CH3 | CH2CH3 | CH | |
| H | SO2N(CH2CH3)2 | H | CH3 | N | |
| H | SO2N(OCH3)CH3 | H | CH3 | N | |
| H | SO2N(OCH3)CH3 | H | CH3 | CH | |
| H | SO2N(OCH3)CH3 | CH3 | CH3 | N | |
| H | SO2N(OCH3)CH3 | CH3 | CH3 | CH | |
| H | SO2CH3 | H | CH3 | CH | |
| H | SOCH3 | H | CH3 | CH | |
| H | SCH3 | H | CH3 | CH | |
| H | SO2CH3 | H | CH3 | N | |
| H | SO2CH2CH3 | H | CH3 | N | |
| CH3 | CH3 | CH3 | OCH3 | N | |
| H | H | CH3 | OCH3 | CH | |
| H | H | CH3 | OCH3 | N | |
| H | CH3 | CH3 | OCH3 | CH | |
| H | CH3 | CH2CH3 | OCH3 | N | |
| H | OCH3 | CH3 | OCH3 | CH | |

TABLE 3a-continued

Structure: pyridine with SO₂NHCONR at position 3, R₄ at position 2; attached to a 6-membered ring (N, Z) with NR₁₄R₁₅ and OCH₂CH₂F substituents.

| R | R₄ | R₁₄ | R₁₅ | Z | m.p. (°C.) |
|---|---|---|---|---|---|
| H | OCH₃ | CH₃ | OCH₃ | N | |
| H | F | CH₃ | OCH₃ | CH | |
| H | Cl | CH₃ | OCH₃ | CH | |
| H | Cl | CH₃ | OCH₃ | N | |
| H | Br | CH₃ | OCH₃ | CH | |
| H | Br | CH₃ | OCH₃ | N | |
| H | SO₂N(CH₃)₂ | CH₃ | OCH₃ | CH | |
| H | SO₂N(CH₃)H | CH₃ | OCH₃ | N | |
| H | SO₂CH₃ | CH₃ | OCH₃ | CH | |
| H | SO₂CH₃ | CH₃ | OCH₃ | N | |
| H | SO₂CH₂CH₃ | CH₂CH₃ | OCH₂CH₃ | N | |
| H | SO₂CH₃ | H | CH₃ | N | |
| H | OCH₂CH₃ | CH₃ | OCH₃ | N | |
| CH₃ | SO₂N(CH₃)₂ | CH₃ | OCH₃ | N | |

TABLE 3b

Structure: pyridine-SO₂NHCONR with ring bearing NR₁₄R₁₅ and OCH₂CHF₂.

| R | R₄ | R₁₄ | R₁₅ | Z | m.p. (°C.) |
|---|---|---|---|---|---|
| CH₃ | CH₃ | H | CH₃ | N | |
| H | CH₃ | H | CH₃ | N | |
| H | CH₃ | H | CH₃ | CH | |
| H | CH₂CH₃ | H | CH₃ | N | |
| H | CH₂CH₃ | H | CH₂CH₃ | CH | |
| H | OCH₃ | H | CH₃ | CH | |
| H | OCH₃ | H | CH₃ | N | |
| H | OCH₃ | CH₃ | CH₃ | N | |
| H | OCH₂CH₃ | H | CH₃ | N | |
| H | F | H | CH₃ | N | |
| H | Cl | H | CH₃ | CH | |
| H | Br | H | CH₃ | CH | |
| H | Br | CH₃ | CH₃ | N | |
| H | SO₂N(CH₃)₂ | H | CH₃ | CH | |
| H | SO₂N(CH₃)₂ | H | CH₃ | N | |
| H | SO₂N(CH₃)₂ | CH₃ | CH₃ | CH | |
| H | SO₂N(CH₃)₂ | CH₃ | CH₂CH₃ | N | |
| H | SO₂N(CH₃)₂ | CH₂CH₃ | CH₂CH₃ | CH | |
| H | SO₂N(CH₂CH₃)₂ | H | CH₃ | N | |
| H | SO₂N(OCH₃)CH₃ | H | CH₃ | N | |
| H | SO₂N(OCH₃)CH₃ | H | CH₃ | CH | |
| H | SO₂N(OCH₃)CH₃ | CH₃ | CH₃ | N | |
| H | SO₂N(OCH₃)CH₃ | CH₃ | CH₃ | CH | |
| H | SO₂CH₃ | H | CH₃ | CH | |
| H | SO₂CH₃ | H | CH₃ | N | |
| H | SO₂CH₂CH₃ | H | CH₃ | N | |
| CH₃ | CH₃ | CH₃ | OCH₃ | N | |
| H | H | CH₃ | OCH₃ | N | |
| H | H | CH₃ | OCH₃ | CH | |
| H | CH₃ | H | CH₂CN | N | |
| H | CH₃ | CH₂CH₃ | OCH₃ | N | |
| H | OCH₃ | CH₃ | OCH₃ | N | |
| H | F | CH₃ | OCH₃ | CH | |
| H | Cl | CH₃ | OCH₃ | CH | |
| H | Cl | CH₃ | OCH₃ | N | |
| H | Cl | CH₃ | OCH₂CH₃ | N | |
| H | Br | CH₃ | OCH₃ | N | |
| H | SO₂N(CH₃)₂ | CH₃ | OCH₃ | CH | |
| H | SO₂N(CH₃)H | CH₃ | OCH₃ | N | |
| H | SO₂CH₃ | CH₃ | OCH₃ | CH | |
| H | SO₂CH₃ | CH₃ | OCH₂CH₃ | N | |

TABLE 3b-continued

| R | R₄ | R₁₄ | R₁₅ | Z | m.p. (°C.) |
|---|---|---|---|---|---|
| H | SO₂CH₂CH₃ | CH₃ | OCH₃ | N | |
| H | SO₂CH₃ | H | CH₃ | N | |
| CH₃ | SO₂N(CH₃)₂ | CH₃ | OCH₃ | N | |

TABLE 3c

Structure: pyridine-SO₂NHCONR with ring bearing NR₁₄R₁₅ and OCH₂CF₃.

| R | R₄ | R₁₄ | R₁₅ | Z | m.p. (°C.) |
|---|---|---|---|---|---|
| CH₃ | CH₃ | H | CH₃ | N | |
| H | CH₃ | H | CH₃ | N | |
| H | CH₃ | H | CH₃ | CH | |
| H | CH₂CH₃ | H | CH₃ | N | |
| H | CH₂CH₃ | H | CH₂CH₃ | CH | |
| H | OCH₃ | H | CH₃ | CH | |
| H | OCH₃ | H | CH₃ | N | |
| H | OCH₃ | CH₃ | CH₃ | N | |
| H | OCH₂CH₃ | H | CH₃ | N | |
| H | F | H | CH₃ | N | |
| H | Cl | H | CH₃ | CH | |
| H | Br | H | CH₃ | CH | |
| H | Br | CH₃ | CH₃ | N | |
| H | SO₂N(CH₃)₂ | H | CH₃ | CH | |
| H | SO₂N(CH₃)₂ | H | CH₃ | N | |
| H | SO₂N(CH₃)₂ | CH₃ | CH₃ | CH | |
| H | SO₂N(CH₃)₂ | CH₃ | CH₂CH₃ | N | |
| H | SO₂N(CH₃)₂ | CH₂CH₃ | CH₂CH₃ | CH | |
| H | SO₂N(CH₂CH₃)₂ | H | CH₃ | N | |
| H | SO₂N(OCH₃)CH₃ | H | CH₃ | N | |
| H | SO₂N(OCH₃)CH₃ | H | CH₃ | CH | |
| H | SO₂N(OCH₃)CH₃ | CH₃ | CH₃ | N | |
| H | SO₂N(OCH₃)CH₃ | CH₃ | CH₃ | CH | |
| H | SO₂CH₃ | H | CH₃ | CH | |
| H | SO₂CH₃ | H | CH₃ | N | |
| H | SO₂CH₂CH₃ | H | CH₃ | N | |
| CH₃ | CH₃ | CH₃ | OCH₃ | N | |
| H | H | CH₃ | OCH₃ | N | |
| H | CH₃ | H | CH₂CN | N | |
| H | CH₃ | CH₂CH₃ | OCH₃ | N | |
| H | OCH₃ | CH₃ | OCH₃ | CH | |
| H | F | CH₃ | OCH₃ | CH | |
| H | F | H | CH₂CN | N | |
| H | Cl | CH₃ | OCH₃ | N | |
| H | Br | CH₃ | OCH₃ | CH | |
| H | SO₂N(CH₃)₂ | CH₃ | OCH₃ | N | |
| H | SO₂N(CH₃)H | CH₃ | OCH₃ | N | |
| H | SO₂CH₃ | CH₃ | OCH₃ | CH | |
| H | SO₂CH₃ | CH₃ | OCH₂CH₃ | N | |
| H | SO₂CH₂CH₃ | CH₃ | OCH₃ | N | |
| H | SO₂CH₃ | H | CH₃ | N | |
| H | OCH₂CH₃ | CH₃ | OCH₃ | CH | |

TABLE 4a

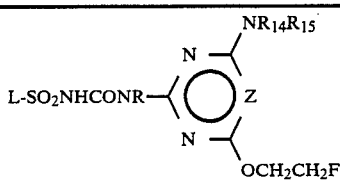

| L R | R$_5$ | R$_{14}$ | R$_{15}$ | Z | m.p. (°C.) |
|---|---|---|---|---|---|
| L-4 H | CH$_3$ | H | CH$_3$ | N | |
| L-4 H | CH$_3$ | H | CH$_3$ | CH | |
| L-4 H | CH$_2$CH$_3$ | H | CH$_3$ | CH | |
| L-4 H | CH$_2$CH$_2$CH$_3$ | CH$_3$ | CH$_3$ | N | |
| L-4 H | F | H | CH$_3$ | CH | |
| L-4 H | F | H | CH$_2$CH$_3$ | N | |
| L-4 H | Cl | CH$_3$ | CH$_3$ | CH | |
| L-4 H | Cl | CH$_2$CH$_3$ | CH$_3$ | N | |
| L-4 H | Br | H | CH$_3$ | N | |
| L-4 H | NO$_2$ | H | CH$_3$ | N | |
| L-4 H | NO$_2$ | CH$_3$ | CH$_3$ | CH | |
| L-4 H | CO$_2$CH$_3$ | H | CH$_3$ | CH | |
| L-4 H | CO$_2$CH$_3$ | H | CH$_3$ | N | |
| L-4 H | CO$_2$CH$_3$ | H | CH$_2$CH$_3$ | CH | |
| L-4 H | CO$_2$CH$_3$ | CH$_3$ | CH$_3$ | CH | |
| L-4 H | CO$_2$CH$_2$CH$_3$ | H | CH$_3$ | N | |
| L-4 H | CO$_2$CH$_2$CH$_3$ | CH$_2$CH$_3$ | CH$_3$ | N | |
| L-4 H | CO$_2$CH$_2$CH$_2$CH$_3$ | H | CH$_3$ | N | |
| L-4 H | CO$_2$CH$_2$CH$_2$CH$_2$CH$_3$ | H | CH$_3$ | N | |
| L-4 H | CO$_2$CH$_2$CH$_2$OCH$_3$ | H | CH$_3$ | N | |
| L-4 H | CO$_2$CH$_2$CH$_2$Cl | H | CH$_3$ | N | |
| L-4 H | CO$_2$CH$_2$CH=CH$_2$ | H | CH$_3$ | CH | |
| L-4 H | CO$_2$CH$_2$CH=CH$_2$ | H | CH$_3$ | N | |
| L-4 H | SO$_2$N(CH$_3$)$_2$ | H | CH$_3$ | CH | |
| L-4 H | SO$_2$N(CH$_3$)$_2$ | H | CH$_3$ | N | |
| L-4 H | SO$_2$N(CH$_3$)$_2$ | CH$_3$ | CH$_3$ | N | |
| L-4 H | SO$_2$N(OCH$_3$)CH$_3$ | H | CH$_3$ | N | |
| L-4 H | SCH$_3$ | H | CH$_3$ | N | |
| L-4 H | CH$_3$ | CH$_3$ | OCH$_3$ | CH | |
| L-4 H | CH$_2$CH$_3$ | CH$_3$ | OCH$_3$ | N | |
| L-4 H | CH$_3$ | CH$_3$ | CH$_2$CN | N | |
| L-4 H | F | CH$_3$ | OCH$_3$ | N | |
| L-4 H | F | H | CH$_3$ | N | |
| L-4 H | Cl | CH$_3$ | OCH$_3$ | N | |
| L-4 H | Br | CH$_3$ | OCH$_3$ | N | |
| L-4 H | NO$_2$ | CH$_3$ | OCH$_3$ | CH | |
| L-4 H | CO$_2$CH$_3$ | CH$_3$ | OCH$_3$ | CH | |
| L-4 H | CO$_2$CH$_3$ | CH$_3$ | OCH$_3$ | N | |
| L-4 CH$_3$ | CO$_2$CH$_2$CH$_3$ | CH$_3$ | OCH$_3$ | N | |
| L-4 CH$_3$ | CO$_2$CH$_2$CH=CH$_2$ | CH$_3$ | OCH$_3$ | CH | |
| L-4 H | CO$_2$CH$_2$C≡CH | H | CH$_3$ | N | |
| L-4 H | SO$_2$N(CH$_3$)$_2$ | CH$_3$ | OCH$_3$ | N | |
| L-4 H | SO$_2$N(CH$_3$)$_2$ | CH$_3$ | CH$_2$CN | N | |
| L-4 CH$_3$ | SO$_2$N(CH$_2$CH$_3$)$_2$ | CH$_3$ | OCH$_3$ | N | |
| L-4 H | SO$_2$N(OCH$_3$)CH$_3$ | CH$_3$ | OCH$_3$ | CH | |
| L-4 H | SO$_2$N(CH$_3$)H | CH$_3$ | OCH$_3$ | N | |
| L-4 H | SO$_2$N(CH$_3$)H | CH$_3$ | OCH$_2$CH$_3$ | N | |
| L-4 H | SO$_2$CH$_3$ | CH$_3$ | OCH$_3$ | N | |
| L-4 CH$_3$ | SO$_2$CH$_2$CH$_3$ | CH$_3$ | OCH$_3$ | CH | |
| L-4 H | SO$_2$CH$_2$CH$_3$ | CH$_3$ | CH$_2$CN | N | |
| L-4 H | S(O)CH$_3$ | H | CH$_3$ | N | |

TABLE 4b

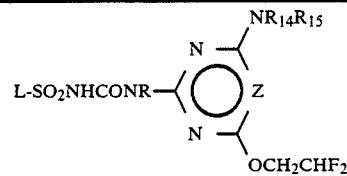

| L R | R$_5$ | R$_{14}$ | R$_{15}$ | Z | m.p. (°C.) |
|---|---|---|---|---|---|
| L-4 H | CH$_3$ | H | CH$_3$ | N | |
| L-4 H | CH$_3$ | H | CH$_3$ | CH | |
| L-4 H | CH$_2$CH$_3$ | H | CH$_3$ | CH | |
| L-4 H | CH$_2$CH$_2$CH$_3$ | CH$_3$ | CH$_3$ | N | |
| L-4 H | F | H | CH$_3$ | CH | |
| L-4 H | F | H | CH$_2$CH$_3$ | N | |
| L-4 H | Cl | CH$_3$ | CH$_3$ | CH | |
| L-4 H | Cl | CH$_2$CH$_3$ | CH$_3$ | N | |
| L-4 H | Br | H | CH$_3$ | N | |
| L-4 H | NO$_2$ | H | CH$_3$ | N | |
| L-4 H | NO$_2$ | CH$_3$ | CH$_3$ | CH | |
| L-4 H | CO$_2$CH$_3$ | H | CH$_3$ | CH | |
| L-4 H | CO$_2$CH$_3$ | H | CH$_3$ | N | |
| L-4 H | CO$_2$CH$_3$ | H | CH$_2$CH$_3$ | CH | |
| L-4 H | CO$_2$CH$_3$ | CH$_3$ | CH$_3$ | CH | |
| L-4 H | CO$_2$CH$_2$CH$_3$ | H | CH$_3$ | N | |
| L-4 H | CO$_2$CH$_2$CH$_3$ | CH$_2$CH$_3$ | CH$_3$ | N | |
| L-4 H | CO$_2$CH$_2$CH$_2$CH$_3$ | H | CH$_3$ | N | |
| L-4 H | CO$_2$CH$_2$CH$_2$CH$_2$CH$_3$ | H | CH$_3$ | N | |
| L-4 H | CO$_2$CH$_2$CH$_2$OCH$_3$ | H | CH$_3$ | N | |
| L-4 H | CO$_2$CH$_2$CH$_2$Cl | H | CH$_3$ | N | |
| L-4 H | CO$_2$CH$_2$CH=CH$_2$ | H | CH$_3$ | CH | |
| L-4 H | CO$_2$CH$_2$CH=CH$_2$ | H | CH$_3$ | N | |
| L-4 H | SO$_2$N(CH$_3$)$_2$ | H | CH$_3$ | CH | |
| L-4 H | SO$_2$N(CH$_3$)$_2$ | H | CH$_3$ | N | |
| L-4 H | SO$_2$N(CH$_3$)$_2$ | CH$_3$ | CH$_3$ | CH | |
| L-4 H | SOCH$_3$ | H | CH$_3$ | N | |
| L-4 H | SOCH$_3$ | H | CH$_3$ | N | |
| L-4 H | CH$_3$ | CH$_3$ | OCH$_3$ | CH | |
| L-4 H | CH$_2$CH$_3$ | CH$_3$ | OCH$_3$ | N | |
| L-4 H | CH$_3$ | CH$_3$ | CH$_2$CN | N | |
| L-4 H | F | CH$_3$ | OCH$_3$ | N | |
| L-4 H | F | H | CH$_3$ | N | |
| L-4 H | Cl | CH$_3$ | OCH$_3$ | N | |
| L-4 H | Br | CH$_3$ | OCH$_3$ | N | |
| L-4 H | NO$_2$ | CH$_3$ | OCH$_3$ | CH | |
| L-4 H | CO$_2$CH$_3$ | CH$_3$ | OCH$_3$ | CH | |
| L-4 H | CO$_2$CH$_3$ | CH$_3$ | OCH$_3$ | N | |
| L-4 CH$_3$ | CO$_2$CH$_2$CH$_3$ | CH$_3$ | OCH$_3$ | N | |
| L-4 CH$_3$ | CO$_2$CH$_2$CHCH$_2$ | CH$_3$ | OCH$_3$ | CH | |
| L-4 CH$_3$ | SO$_2$N(CH$_3$)$_2$ | CH$_3$ | OCH$_3$ | N | |
| L-4 CH$_3$ | SO$_2$N(CH$_3$)$_2$ | CH$_3$ | OCH$_3$ | CH | |
| L-4 CH$_3$ | SO$_2$N(CH$_2$CH$_3$)$_2$ | CH$_3$ | OCH$_3$ | N | |
| L-4 H | SO$_2$N(OCH$_3$)CH$_3$ | CH$_3$ | OCH$_3$ | N | |
| L-4 H | SO$_2$N(CH$_3$)H | CH$_3$ | OCH$_3$ | N | |
| L-4 CH$_3$ | SO$_2$CH$_3$ | CH$_3$ | OCH$_3$ | N | |
| L-4 CH$_3$ | SO$_2$CH$_2$CH$_3$ | CH$_3$ | OCH$_3$ | CH | |
| L-4 CH$_3$ | SO$_2$CH$_2$CH$_2$CH$_3$ | CH$_3$ | OCH$_3$ | N | |
| L-4 H | SCH$_3$ | CH$_3$ | CH$_2$CN | N | |

TABLE 4c

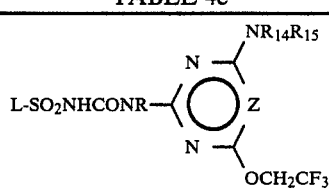

| L | R | R$_5$ | R$_{14}$ | R$_{15}$ | Z | m.p.(°C.) |
|---|---|---|---|---|---|---|
| L-4 | H | CH$_3$ | H | CH$_3$ | N | |
| L-4 | H | CH$_3$ | H | CH$_3$ | CH | |
| L-4 | H | CH$_2$CH$_3$ | H | CH$_3$ | CH | |
| L-4 | H | CH$_2$CH$_2$CH$_3$ | CH$_3$ | CH$_3$ | N | |
| L-4 | H | F | H | CH$_3$ | CH | |

TABLE 4c-continued

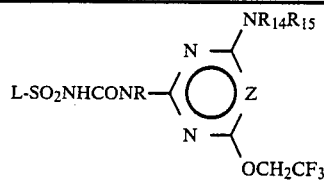

| L | R | $R_5$ | $R_{14}$ | $R_{15}$ | Z | m.p.(°C.) |
|---|---|---|---|---|---|---|
| L-4 | H | F | H | $CH_2CH_3$ | N | |
| L-4 | H | Cl | $CH_3$ | $CH_3$ | CH | |
| L-4 | H | Cl | $CH_2CH_3$ | $CH_3$ | N | |
| L-4 | H | Br | H | $CH_3$ | N | |
| L-4 | H | $NO_2$ | H | $CH_3$ | N | |
| L-4 | H | $NO_2$ | $CH_3$ | $CH_3$ | CH | |
| L-4 | H | $CO_2CH_3$ | H | $CH_3$ | CH | |
| L-4 | H | $CO_2CH_3$ | H | $CH_3$ | N | |
| L-4 | H | $CO_2CH_3$ | H | $CH_2CH_3$ | CH | |
| L-4 | H | $CO_2CH_3$ | $CH_3$ | $CH_3$ | CH | |
| L-4 | H | $CO_2CH_2CH_3$ | H | $CH_3$ | N | |
| L-4 | H | $CO_2CH_2CH_3$ | $CH_2CH_3$ | $CH_3$ | N | |
| L-4 | H | $CO_2CH_2CH_2CH_3$ | H | $CH_3$ | N | |
| L-4 | H | $CO_2CH_2CH_2CH_2CH_3$ | H | $CH_3$ | N | |
| L-4 | H | $CO_2CH_2CH_2OCH_3$ | H | $CH_3$ | N | |
| L-4 | H | $CO_2CH_2CH_2Cl$ | H | $CH_3$ | N | |
| L-4 | H | $CO_2CH_2CH=CH_2$ | H | $CH_3$ | CH | |
| L-4 | H | $CO_2CH_2CH=CH_2$ | H | $CH_3$ | N | |
| L-4 | H | $SO_2N(CH_3)_2$ | H | $CH_3$ | CH | |
| L-4 | H | $SO_2N(CH_3)_2$ | H | $CH_3$ | N | |
| L-4 | H | $SO_2N(CH_3)_2$ | $CH_3$ | $CH_3$ | CH | |
| L-4 | H | $SOCH_3$ | H | $CH_3$ | N | |
| L-4 | H | $CH_3$ | $CH_3$ | $OCH_3$ | CH | |
| L-4 | H | $CH_3$ | $CH_3$ | $OCH_3$ | N | |
| L-4 | H | $CH_3$ | $CH_3$ | $CH_2CN$ | N | |
| L-4 | H | F | $CH_3$ | $OCH_3$ | N | |
| L-4 | H | Cl | $CH_3$ | $OCH_3$ | CH | |
| L-4 | H | Cl | $CH_3$ | $OCH_2CH_3$ | N | |
| L-4 | H | Br | $CH_3$ | $OCH_3$ | N | |
| L-4 | H | $NO_2$ | $CH_3$ | $OCH_3$ | CH | |
| L-4 | H | $CO_2CH_3$ | $CH_3$ | $OCH_3$ | CH | |
| L-4 | H | $CO_2CH_3$ | $CH_3$ | $OCH_3$ | N | |
| L-4 | H | $CO_2CH_3$ | $CH_3$ | $OCH_2CH_3$ | N | |
| L-4 | $CH_3$ | $CO_2CH_2CH_3$ | $CH_3$ | $OCH_3$ | N | |
| L-4 | $CH_3$ | $CO_2CH_2CH=CH_2$ | $CH_3$ | $OCH_3$ | N | |
| L-4 | $CH_3$ | $SO_2N(CH_3)_2$ | $CH_3$ | $OCH_3$ | N | |
| L-4 | H | $SO_2N(CH_3)_2$ | $CH_3$ | $CH_2CN$ | N | |
| L-4 | H | $SO_2N(OCH_3)CH_3$ | $CH_3$ | $OCH_3$ | CH | |
| L-4 | H | $SO_2N(CH_3)H$ | H | $CH_3$ | N | |
| L-4 | H | $SO_2N(CH_3)H$ | $CH_3$ | $OCH_3$ | N | |
| L-4 | H | $SO_2CH_3$ | $CH_3$ | $OCH_3$ | CH | |
| L-4 | $CH_3$ | $SO_2CH_3$ | $CH_3$ | $OCH_3$ | N | |
| L-4 | H | $SO_2CH_2CH_3$ | $CH_3$ | $CH_2CN$ | N | |
| L-4 | H | $S(O)CH_3$ | H | $CH_3$ | N | |

TABLE 5a

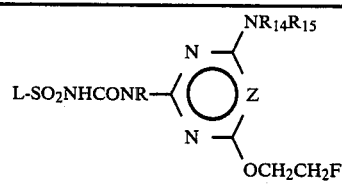

| L | R | $R_5$ | $R_{14}$ | $R_{15}$ | Z | m.p.(°C.) |
|---|---|---|---|---|---|---|
| L-5 | H | $CH_3$ | H | $CH_3$ | N | |
| L-5 | H | $CH_3$ | H | $CH_3$ | CH | |
| L-5 | H | $CH_2CH_3$ | H | $CH_3$ | CH | |
| L-5 | H | $CH_2CH_2CH_3$ | $CH_3$ | $CH_3$ | N | |
| L-5 | H | F | H | $CH_3$ | CH | |
| L-5 | H | F | H | $CH_2CH_3$ | N | |
| L-5 | H | Cl | $CH_3$ | $CH_3$ | CH | |
| L-5 | H | Cl | $CH_2CH_3$ | $CH_3$ | N | |
| L-5 | H | Br | H | $CH_3$ | N | |
| L-5 | H | $NO_2$ | H | $CH_3$ | N | |
| L-5 | H | $NO_2$ | $CH_3$ | $CH_3$ | CH | |
| L-5 | H | $CO_2CH_3$ | H | $CH_3$ | CH | |
| L-5 | H | $CO_2CH_3$ | H | $CH_3$ | N | |

TABLE 5a-continued

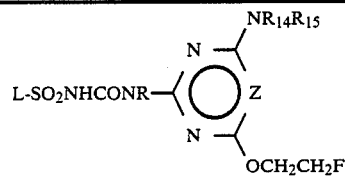

| L | R | $R_5$ | $R_{14}$ | $R_{15}$ | Z | m.p.(°C.) |
|---|---|---|---|---|---|---|
| L-5 | H | $CO_2CH_3$ | H | $CH_2CH_3$ | CH | |
| L-5 | H | $CO_2CH_3$ | $CH_3$ | $CH_3$ | CH | |
| L-5 | H | $CO_2CH_2CH_3$ | H | $CH_3$ | N | |
| L-5 | H | $CO_2CH_2CH_3$ | $CH_2CH_3$ | $CH_3$ | N | |
| L-5 | H | $CO_2CH_2CH_2CH_3$ | H | $CH_3$ | N | |
| L-5 | H | $CO_2CH_2CH_2CH_2CH_3$ | H | $CH_3$ | N | |
| L-5 | H | $CO_2CH_2CH_2OCH_3$ | H | $CH_3$ | N | |
| L-5 | H | $CO_2CH_2CH_2Cl$ | H | $CH_3$ | N | |
| L-5 | H | $CO_2CH_2CH=CH_2$ | H | $CH_3$ | CH | |
| L-5 | H | $CO_2CH_2CH=CH_2$ | H | $CH_3$ | N | |
| L-5 | H | $SO_2N(CH_3)_2$ | H | $CH_3$ | CH | |
| L-5 | H | $SO_2N(CH_3)_2$ | H | $CH_3$ | N | |
| L-5 | H | $SO_2N(CH_3)_2$ | $CH_3$ | $CH_3$ | CH | |
| L-5 | H | $SCH_3$ | H | $CH_3$ | N | |
| L-5 | H | $SOCH_3$ | H | $CH_3$ | N | |
| L-5 | H | $SO_2N(OCH_3)CH_3$ | H | $CH_3$ | N | |
| L-5 | H | $CH_3$ | $CH_3$ | $OCH_3$ | CH | |
| L-5 | H | $CH_3$ | $CH_3$ | $OCH_3$ | N | |
| L-5 | H | $CH_3$ | $CH_3$ | $CH_2CN$ | N | |
| L-5 | H | F | $CH_3$ | $OCH_3$ | N | |
| L-5 | H | F | H | $CH_3$ | N | |
| L-5 | H | Cl | $CH_3$ | $OCH_3$ | N | |
| L-5 | H | Cl | $CH_3$ | $OCH_2CH_3$ | N | |
| L-5 | H | Br | $CH_3$ | $CH_2CN$ | N | |
| L-5 | H | $NO_2$ | $CH_3$ | $OCH_3$ | CH | |
| L-5 | H | $CO_2CH_3$ | $CH_3$ | $OCH_3$ | N | |
| L-5 | $CH_3$ | $CO_2CH_3$ | $CH_3$ | $OCH_3$ | N | |
| L-5 | $CH_3$ | $CO_2CH_2CH=CH_2$ | $CH_3$ | $OCH_3$ | CH | |
| L-5 | $CH_3$ | $CO_2CH_2CH=CH_2$ | $CH_3$ | $OCH_3$ | N | |
| L-5 | H | $CO_2CH_2C\equiv CH$ | $CH_3$ | $OCH_3$ | N | |
| L-5 | $CH_3$ | $SO_2N(CH_3)_2$ | $CH_3$ | $OCH_3$ | N | |
| L-5 | H | $SO_2N(CH_3)_2$ | $CH_3$ | $CH_2CN$ | N | |
| L-5 | H | $SO_2N(CH_3)CH_2CH_3$ | $CH_3$ | $OCH_3$ | CH | |
| L-5 | H | $SO_2N(OCH_3)CH_3$ | $CH_3$ | $OCH_3$ | CH | |
| L-5 | H | $SO_2N(CH_3)H$ | H | $CH_3$ | N | |
| L-5 | H | $SO_2N(CH_3)H$ | $CH_3$ | $OCH_3$ | N | |
| L-5 | H | $SO_2CH_3$ | $CH_3$ | $OCH_3$ | CH | |
| L-5 | $CH_3$ | $SO_2CH_3$ | $CH_3$ | $OCH_3$ | N | |
| L-5 | H | $SO_2CH_2CH_3$ | $CH_3$ | $CH_2CN$ | N | |
| L-5 | H | $SCH_3$ | $CH_3$ | $CH_2CN$ | N | |

TABLE 5b

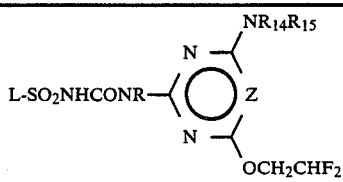

| L | R | $R_5$ | $R_{14}$ | $R_{15}$ | Z | m.p.(°C.) |
|---|---|---|---|---|---|---|
| L-5 | H | $CH_3$ | H | $CH_3$ | N | |
| L-5 | H | $CH_3$ | H | $CH_3$ | CH | |
| L-5 | H | $CH_2CH_3$ | H | $CH_3$ | CH | |
| L-5 | H | $CH_2CH_2CH_3$ | $CH_3$ | $CH_3$ | N | |
| L-5 | H | F | H | $CH_3$ | CH | |
| L-5 | H | F | H | $CH_2CH_3$ | N | |
| L-5 | H | Cl | $CH_3$ | $CH_3$ | CH | |
| L-5 | H | Cl | $CH_2CH_3$ | $CH_3$ | N | |
| L-5 | H | Br | H | $CH_3$ | N | |
| L-5 | H | $NO_2$ | H | $CH_3$ | N | |
| L-5 | H | $NO_2$ | $CH_3$ | $CH_3$ | CH | |
| L-5 | H | $CO_2CH_3$ | H | $CH_3$ | CH | |
| L-5 | H | $CO_2CH_3$ | H | $CH_3$ | N | |
| L-5 | H | $CO_2CH_3$ | H | $CH_2CH_3$ | CH | |
| L-5 | H | $CO_2CH_3$ | $CH_3$ | $CH_3$ | CH | |
| L-5 | H | $CO_2CH_2CH_3$ | H | $CH_3$ | N | |
| L-5 | H | $CO_2CH_2CH_3$ | $CH_2CH_3$ | $CH_3$ | N | |

TABLE 5b-continued

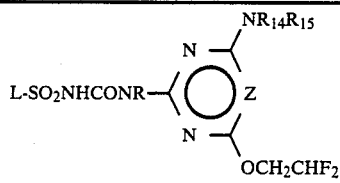

| L | R | $R_5$ | $R_{14}$ | $R_{15}$ | Z | m.p.(°C.) |
|---|---|---|---|---|---|---|
| L-5 | H | $CO_2CH_2CH_2CH_3$ | H | $CH_3$ | N | |
| L-5 | H | $CO_2CH_2CH_2CH_2CH_3$ | H | $CH_3$ | N | |
| L-5 | H | $CO_2CH_2CH_2OCH_3$ | H | $CH_3$ | N | |
| L-5 | H | $CO_2CH_2CH_2Cl$ | H | $CH_3$ | N | |
| L-5 | H | $CO_2CH_2CH=CH_2$ | H | $CH_3$ | CH | |
| L-5 | H | $CO_2CH_2CH=CH_2$ | H | $CH_3$ | N | |
| L-5 | H | $SO_2N(CH_3)_2$ | H | $CH_3$ | CH | |
| L-5 | H | $SO_2N(CH_3)_2$ | H | $CH_3$ | N | |
| L-5 | H | $SO_2N(CH_3)_2$ | $CH_3$ | $CH_3$ | CH | |
| L-5 | H | $SCH_3$ | H | $CH_3$ | N | |
| L-5 | H | $SOCH_3$ | H | $CH_3$ | N | |
| L-5 | H | $CH_3$ | $CH_3$ | $OCH_3$ | CH | |
| L-5 | H | $CH_2CH_3$ | $CH_3$ | $OCH_3$ | N | |
| L-5 | H | $CH_2CH_2CH_3$ | $CH_3$ | $OCH_3$ | CH | |
| L-5 | H | F | $CH_3$ | $OCH_3$ | N | |
| L-5 | H | Cl | $CH_3$ | $OCH_3$ | CH | |
| L-5 | H | Br | $CH_3$ | $OCH_3$ | N | |
| L-5 | H | Br | $CH_3$ | $CH_2CN$ | N | |
| L-5 | H | $CO_2CH_3$ | $CH_3$ | $OCH_3$ | CH | |
| L-5 | H | $CO_2CH_3$ | $CH_3$ | $OCH_3$ | N | |
| L-5 | H | $CO_2CH_3$ | $CH_3$ | $OCH_3CH_3$ | N | |
| L-5 | $CH_3$ | $CO_2CH_2CH_3$ | $CH_3$ | $OCH_3$ | N | |
| L-5 | $CH_3$ | $CO_2CH_2CH=CH_2$ | $CH_3$ | $OCH_3$ | N | |
| L-5 | $CH_3$ | $SO_2N(CH_3)_2$ | $CH_3$ | $OCH_3$ | N | |
| L-5 | $CH_3$ | $SO_2N(CH_3)_2$ | $CH_3$ | $OCH_3$ | CH | |
| L-5 | H | $SO_2N(CH_3)CH_2CH_3$ | $CH_3$ | $OCH_3$ | CH | |
| L-5 | H | $SO_2N(OCH_3)CH_3$ | $CH_3$ | $OCH_3$ | CH | |
| L-5 | H | $SO_2N(CH_3)H$ | H | $CH_3$ | N | |
| L-5 | H | $SO_2N(CH_3)H$ | $CH_3$ | $OCH_2CH_3$ | N | |
| L-5 | H | $SO_2CH_3$ | $CH_3$ | $OCH_3$ | CH | |
| L-5 | $CH_3$ | $SO_2CH_2CH_3$ | $CH_3$ | $OCH_3$ | CH | |
| L-5 | $CH_3$ | $SO_2CH_2CH_2CH_3$ | $CH_3$ | $OCH_3$ | CH | |
| L-5 | H | $SCH_3$ | $CH_3$ | $CH_2CN$ | N | |

TABLE 5c

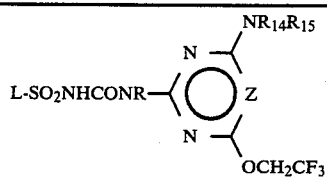

| L | R | $R_5$ | $R_{14}$ | $R_{15}$ | Z | m.p.(°C.) |
|---|---|---|---|---|---|---|
| L-5 | H | $CH_3$ | H | $CH_3$ | N | |
| L-5 | H | $CH_3$ | H | $CH_3$ | CH | |
| L-5 | H | $CH_2CH_3$ | H | $CH_3$ | CH | |
| L-5 | H | $CH_2CH_2CH_3$ | H | $CH_3$ | N | |
| L-5 | H | F | H | $CH_3$ | CH | |
| L-5 | H | F | H | $CH_2CH_3$ | N | |
| L-5 | H | Cl | $CH_3$ | $CH_3$ | CH | |
| L-5 | H | Cl | $CH_2CH_3$ | $CH_3$ | N | |
| L-5 | H | Br | H | $CH_3$ | N | |
| L-5 | H | $NO_2$ | H | $CH_3$ | N | |
| L-5 | H | $NO_2$ | $CH_3$ | $CH_3$ | CH | |
| L-5 | H | $CO_2CH_3$ | H | $CH_3$ | CH | |
| L-5 | H | $CO_2CH_3$ | H | $CH_3$ | N | 211–212(d) |
| L-5 | H | $CO_2CH_3$ | H | $CH_2CH_3$ | CH | |
| L-5 | H | $CO_2CH_3$ | $CH_3$ | $CH_3$ | CH | |
| L-5 | H | $CO_2CH_2CH_3$ | H | $CH_3$ | N | |
| L-5 | H | $CO_2CH_2CH_3$ | $CH_2CH_3$ | $CH_3$ | N | |
| L-5 | H | $CO_2CH_2CH_2CH_3$ | H | $CH_3$ | N | |
| L-5 | H | $CO_2CH_2CH_2CH_2CH_3$ | H | $CH_3$ | N | |
| L-5 | H | $CO_2CH_2CH_2OCH_3$ | H | $CH_3$ | N | |
| L-5 | H | $CO_2CH_2CH_2Cl$ | H | $CH_3$ | N | |
| L-5 | H | $CO_2CH_2CH=CH_2$ | H | $CH_3$ | CH | |
| L-5 | H | $CO_2CH_2CH=CH_2$ | H | $CH_3$ | N | |
| L-5 | H | $SO_2N(CH_3)_2$ | H | $CH_3$ | CH | |

TABLE 5c-continued

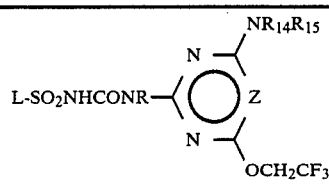

| L | R | $R_5$ | $R_{14}$ | $R_{15}$ | Z | m.p.(°C.) |
|---|---|---|---|---|---|---|
| L-5 | H | $SO_2N(CH_3)_2$ | H | $CH_3$ | N | |
| L-5 | H | $SO_2N(CH_3)_2$ | $CH_3$ | $CH_3$ | CH | |
| L-5 | H | $SOCH_3$ | H | $CH_3$ | N | |
| L-5 | H | $CH_3$ | $CH_3$ | $OCH_3$ | N | |
| L-5 | H | $CH_3$ | $CH_3$ | $CH_2CN$ | N | |
| L-5 | H | $CH_2CH_2CH_3$ | $CH_3$ | $OCH_3$ | CH | |
| L-5 | H | F | H | $CH_3$ | N | |
| L-5 | H | Cl | $CH_3$ | $OCH_3$ | CH | |
| L-5 | H | Cl | $CH_3$ | $OCH_2CH_3$ | N | |
| L-5 | H | Br | $CH_3$ | $CH_2CN$ | N | |
| L-5 | H | $CO_2CH_3$ | $CH_3$ | $OCH_3$ | CH | |
| L-5 | H | $CO_2CH_3$ | $CH_3$ | $OCH_3$ | N | |
| L-5 | $CH_3$ | $CO_2CH_3$ | $CH_3$ | $OCH_3$ | N | |
| L-5 | $CH_3$ | $CO_2CH_2CH_3$ | $CH_3$ | $OCH_3$ | N | |
| L-5 | $CH_3$ | $CO_2CH_2CH=CH_2$ | $CH_3$ | $OCH_3$ | CH | |
| L-5 | H | $CO_2CH_2C\equiv CH$ | H | $CH_3$ | N | |
| L-5 | H | $CO_2CH_2C\equiv CH$ | $CH_3$ | $OCH_3$ | N | |
| L-5 | $CH_3$ | $SO_2N(CH_3)_2$ | $CH_3$ | $OCH_3$ | CH | |
| L-5 | H | $SO_2N(CH_3)CH_2CH_3$ | $CH_3$ | $OCH_3$ | CH | |
| L-5 | H | $SO_2N(OCH_3)CH_3$ | $CH_3$ | $OCH_3$ | CH | |
| L-5 | H | $SO_2N(CH_3)H$ | H | $CH_3$ | N | |
| L-5 | H | $SO_2N(CH_3)H$ | $CH_3$ | $OCH_2CH_3$ | N | |
| L-5 | H | $SO_2CH_3$ | $CH_3$ | $OCH_3$ | CH | |
| L-5 | $CH_3$ | $SO_2CH_2CH_3$ | $CH_3$ | $OCH_3$ | CH | |
| L-5 | $CH_3$ | $SO_2CH_2CH_2CH_3$ | $CH_3$ | $OCH_3$ | CH | |
| L-5 | H | $SCH_3$ | $CH_3$ | $CH_2CN$ | N | |

TABLE 6a

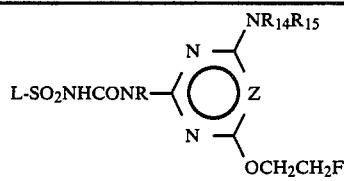

| L | R | $R_5$ | $R_{14}$ | $R_{15}$ | Z | m.p.(°C.) |
|---|---|---|---|---|---|---|
| L-6 | H | $CH_3$ | H | $CH_3$ | N | |
| L-6 | H | $CH_3$ | H | $CH_3$ | CH | |
| L-6 | H | $CH_2CH_3$ | H | $CH_3$ | CH | |
| L-6 | H | $CH_2CH_2CH_3$ | $CH_3$ | $CH_3$ | N | |
| L-6 | H | F | H | $CH_3$ | CH | |
| L-6 | H | F | H | $CH_2CH_3$ | N | |
| L-6 | H | Cl | $CH_3$ | $CH_3$ | CH | |
| L-6 | H | Cl | $CH_2CH_3$ | $CH_3$ | N | |
| L-6 | H | Br | H | $CH_3$ | N | |
| L-6 | H | $NO_2$ | H | $CH_3$ | N | |
| L-6 | H | $NO_2$ | $CH_3$ | $CH_3$ | CH | |
| L-6 | H | $CO_2CH_3$ | H | $CH_3$ | CH | |
| L-6 | H | $CO_2CH_3$ | H | $CH_3$ | N | |
| L-6 | H | $CO_2CH_3$ | H | $CH_2CH_3$ | CH | |
| L-6 | H | $CO_2CH_3$ | $CH_3$ | $CH_3$ | CH | |
| L-6 | H | $CO_2CH_2CH_3$ | H | $CH_3$ | N | |
| L-6 | H | $CO_2CH_2CH_3$ | $CH_2CH_3$ | $CH_3$ | N | |
| L-6 | H | $CO_2CH_2CH_2CH_3$ | H | $CH_3$ | N | |
| L-6 | H | $CO_2CH_2CH_2CH_2CH_3$ | H | $CH_3$ | N | |
| L-6 | H | $CO_2CH_2CH_2OCH_3$ | H | $CH_3$ | N | |
| L-6 | H | $CO_2CH_2CH_2Cl$ | H | $CH_3$ | N | |
| L-6 | H | $CO_2CH_2CH=CH_2$ | H | $CH_3$ | CH | |
| L-6 | H | $CO_2CH_2CH=CH_2$ | H | $CH_3$ | N | |
| L-6 | H | $SO_2N(CH_3)_2$ | H | $CH_3$ | CH | |
| L-6 | H | $SO_2N(CH_3)_2$ | H | $CH_3$ | N | |
| L-6 | H | $SO_2N(CH_3)_2$ | $CH_3$ | $CH_3$ | CH | |
| L-6 | H | $SCH_3$ | H | $CH_3$ | N | |
| L-6 | H | $SOCH_3$ | H | $CH_3$ | N | |
| L-6 | H | $SO_2N(OCH_3)CH_3$ | H | $CH_3$ | N | |
| L-6 | H | $CH_3$ | $CH_3$ | $OCH_3$ | CH | |
| L-6 | H | $CH_3$ | $CH_3$ | $OCH_3$ | N | |

TABLE 6a-continued

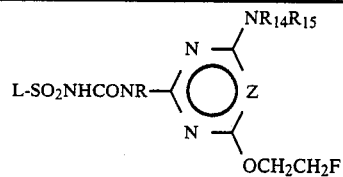

| L | R | R5 | R14 | R15 | Z | m.p.(°C.) |
|---|---|----|-----|-----|---|-----------|
| L-6 | H | CH3 | CH3 | CH2CN | N | |
| L-6 | H | F | CH3 | OCH3 | N | |
| L-6 | H | F | H | CH3 | N | |
| L-6 | H | Cl | CH3 | OCH3 | N | |
| L-6 | H | Cl | CH3 | OCH2CH3 | N | |
| L-6 | H | Br | CH3 | CH2CN | N | |
| L-6 | H | NO2 | CH3 | OCH3 | CH | |
| L-6 | H | CO2CH3 | CH3 | OCH3 | N | |
| L-6 | CH3 | CO2CH3 | CH3 | OCH3 | N | |
| L-6 | H | CO2CH3 | CH3 | OCH2CH3 | N | |
| L-6 | CH3 | CO2CH2CH=CH2 | CH3 | OCH3 | CH | |
| L-6 | H | CO2CH2C≡CH | CH3 | OCH3 | N | |
| L-6 | CH3 | SO2N(CH3)2 | CH3 | OCH3 | CH | |
| L-6 | H | SO2N(OCH3)CH3 | CH3 | OCH3 | CH | |
| L-6 | H | SO2N(CH3)H | H | CH3 | N | |
| L-6 | H | SO2N(CH3)H | CH3 | OCH2CH3 | N | |
| L-6 | CH3 | SO2CH3 | CH3 | OCH3 | N | |
| L-6 | H | SO2CH2CH3 | CH3 | CH2CN | N | |
| L-6 | CH3 | SO2CH2CH2CH3 | CH3 | OCH3 | N | |
| L-6 | H | S(O)CH3 | H | CH3 | N | |

TABLE 6b

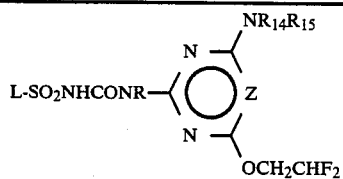

| L | R | R5 | R14 | R15 | Z | m.p.(°C.) |
|---|---|----|-----|-----|---|-----------|
| L-6 | H | CH3 | H | CH3 | N | |
| L-6 | H | CH3 | H | CH3 | CH | |
| L-6 | H | CH2CH3 | H | CH3 | CH | |
| L-6 | H | CH2CH2CH3 | CH3 | CH3 | N | |
| L-6 | H | F | H | CH3 | CH | |
| L-6 | H | F | H | CH2CH3 | N | |
| L-6 | H | Cl | CH3 | CH3 | CH | |
| L-6 | H | Cl | CH2CH3 | CH3 | N | |
| L-6 | H | Br | H | CH3 | N | |
| L-6 | H | NO2 | H | CH3 | N | |
| L-6 | H | NO2 | CH3 | CH3 | CH | |
| L-6 | H | CO2CH3 | H | CH3 | CH | |
| L-6 | H | CO2CH3 | H | CH3 | N | |
| L-6 | H | CO2CH3 | H | CH2CH3 | CH | |
| L-6 | H | CO2CH3 | CH3 | CH3 | CH | |
| L-6 | H | CO2CH2CH3 | H | CH3 | N | |
| L-6 | H | CO2CH2CH3 | CH2CH3 | CH3 | N | |
| L-6 | H | CO2CH2CH2CH3 | H | CH3 | N | |
| L-6 | H | CO2CH2CH2CH2CH3 | H | CH3 | N | |
| L-6 | H | CO2CH2CH2OCH3 | H | CH3 | N | |
| L-6 | H | CO2CH2CH2Cl | H | CH3 | N | |
| L-6 | H | CO2CH2CH=CH2 | H | CH3 | CH | |
| L-6 | H | CO2CH2CH=CH2 | H | CH3 | N | |
| L-6 | H | SO2N(CH3)2 | H | CH3 | CH | |
| L-6 | H | SO2N(CH3)2 | H | CH3 | N | |
| L-6 | H | SO2N(CH3)2 | CH3 | CH3 | CH | |
| L-6 | H | SCH3 | H | CH3 | N | |
| L-6 | H | CH3 | CH3 | OCH3 | CH | |
| L-6 | H | CH3 | CH3 | CH2CN | N | |
| L-6 | H | F | CH3 | OCH3 | N | |
| L-6 | H | Cl | CH3 | OCH3 | CH | |
| L-6 | H | Cl | CH3 | OCH2CH3 | N | |
| L-6 | H | Br | CH3 | OCH3 | N | |
| L-6 | H | NO2 | CH3 | OCH3 | CH | |
| L-6 | H | CO2CH3 | CH3 | OCH3 | N | |
| L-6 | CH3 | CO2CH3 | CH3 | OCH3 | N | |
| L-6 | CH3 | CO2CH2CH3 | CH3 | OCH3 | N | |

TABLE 6b-continued

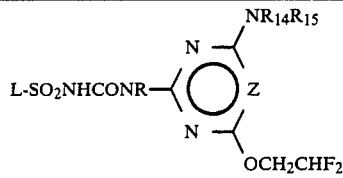

| L | R | R_5 | R_14 | R_15 | Z | m.p.(°C.) |
|---|---|---|---|---|---|---|
| L-6 | $CH_3$ | $CO_2CH_2CH=CH_2$ | $CH_3$ | $OCH_3$ | CH | |
| L-6 | H | $CO_2CH_2C\equiv CH$ | H | $CH_3$ | N | |
| L-6 | $CH_3$ | $SO_2N(CH_3)_2$ | $CH_3$ | $OCH_3$ | N | |
| L-6 | H | $SO_2N(CH_3)_2$ | $CH_3$ | $CH_2CN$ | N | |
| L-6 | H | $SO_2N(CH_3)CH_2CH_3$ | $CH_3$ | $OCH_3$ | CH | |
| L-6 | H | $SO_2N(OCH_3)CH_3$ | $CH_3$ | $OCH_3$ | CH | |
| L-6 | H | $SO_2N(OCH_3)CH_3$ | $CH_3$ | $OCH_3$ | N | |
| L-6 | H | $SO_2N(CH_3)H$ | $CH_3$ | $OCH_3$ | N | |
| L-6 | H | $SO_2N(CH_3)H$ | $CH_3$ | $OCH_2CH_3$ | N | |
| L-6 | $CH_3$ | $SO_2CH_3$ | $CH_3$ | $OCH_3$ | N | |
| L-6 | H | $SO_2CH_2CH_3$ | $CH_3$ | $CH_2CN$ | N | |
| L-6 | $CH_3$ | $SO_2CH_2CH_2CH_3$ | $CH_3$ | $OCH_3$ | N | |
| L-6 | H | $S(O)CH_3$ | H | $CH_3$ | N | |

TABLE 6c

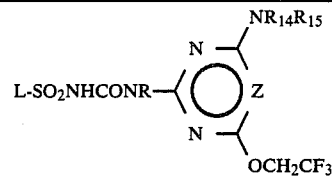

| L | R | R_5 | R_14 | R_15 | Z | m.p.(°C.) |
|---|---|---|---|---|---|---|
| L-6 | H | $CH_3$ | H | $CH_3$ | N | |
| L-6 | H | $CH_3$ | H | $CH_3$ | CH | |
| L-6 | H | $CH_2CH_3$ | H | $CH_3$ | CH | |
| L-6 | H | $CH_2CH_2CH_3$ | $CH_3$ | $CH_3$ | N | |
| L-6 | H | F | H | $CH_3$ | CH | |
| L-6 | H | F | H | $CH_2CH_3$ | N | |
| L-6 | H | Cl | $CH_3$ | $CH_3$ | CH | |
| L-6 | H | Cl | $CH_2CH_3$ | $CH_3$ | N | |
| L-6 | H | Br | H | $CH_3$ | N | |
| L-6 | H | $NO_2$ | H | $CH_3$ | N | |
| L-6 | H | $NO_2$ | $CH_3$ | $CH_3$ | CH | |
| L-6 | H | $CO_2CH_3$ | H | $CH_3$ | CH | |
| L-6 | H | $CO_2CH_3$ | H | $CH_3$ | N | |
| L-6 | H | $CO_2CH_3$ | H | $CH_2CH_3$ | CH | |
| L-6 | H | $CO_2CH_3$ | $CH_3$ | $CH_3$ | CH | |
| L-6 | H | $CO_2CH_2CH_3$ | H | $CH_3$ | N | |
| L-6 | H | $CO_2CH_2CH_3$ | $CH_2CH_3$ | $CH_3$ | N | |
| L-6 | H | $CO_2CH_2CH_2CH_3$ | H | $CH_3$ | N | |
| L-6 | H | $CO_2CH_2CH_2CH_2CH_3$ | H | $CH_3$ | N | |
| L-6 | H | $CO_2CH_2CH_2OCH_3$ | H | $CH_3$ | N | |
| L-6 | H | $CO_2CH_2CH_2Cl$ | H | $CH_3$ | N | |
| L-6 | H | $CO_2CH_2CH=CH_2$ | H | $CH_3$ | CH | |
| L-6 | H | $CO_2CH_2CH=CH_2$ | H | $CH_3$ | N | |
| L-6 | H | $SO_2N(CH_3)_2$ | H | $CH_3$ | CH | |
| L-6 | H | $SO_2N(CH_3)_2$ | H | $CH_3$ | N | |
| L-6 | H | $SO_2N(CH_3)_2$ | $CH_3$ | $CH_3$ | CH | |
| L-6 | H | $CH_3$ | $CH_3$ | $OCH_3$ | CH | |
| L-6 | H | $CH_3$ | $CH_3$ | $OCH_3$ | N | |
| L-6 | H | $CH_3$ | $CH_3$ | $CH_2CN$ | N | |
| L-6 | H | F | $CH_3$ | $OCH_3$ | N | |
| L-6 | H | Cl | $CH_3$ | $OCH_3$ | CH | |
| L-6 | H | Cl | $CH_3$ | $OCH_3$ | N | |
| L-6 | H | Br | $CH_3$ | $OCH_3$ | N | |
| L-6 | H | Br | $CH_3$ | $CH_2CN$ | N | |
| L-6 | H | $CO_2CH_3$ | $CH_3$ | $OCH_3$ | CH | |
| L-6 | H | $CO_2CH_3$ | $CH_3$ | $OCH_3$ | N | |
| L-6 | H | $CO_2CH_3$ | $CH_3$ | $OCH_2CH_3$ | N | |
| L-6 | $CH_3$ | $CO_2CH_2CH_3$ | $CH_3$ | $OCH_3$ | N | |
| L-6 | $CH_3$ | $CO_2CH_2CH=CH_2$ | $CH_3$ | $OCH_3$ | N | |
| L-6 | $CH_3$ | $SO_2N(CH_3)_2$ | $CH_3$ | $OCH_3$ | N | |
| L-6 | H | $SO_2N(CH_3)_2$ | $CH_3$ | $CH_2CN$ | N | |
| L-6 | $CH_3$ | $SO_2N(CH_2CH_3)_2$ | $CH_3$ | $OCH_3$ | N | |
| L-6 | H | $SO_2N(OCH_3)CH_3$ | $CH_3$ | $OCH_3$ | CH | |
| L-6 | H | $SO_2N(CH_3)H$ | H | $CH_3$ | N | |

TABLE 6c-continued

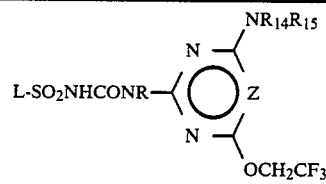

| L | R | R5 | R14 | R15 | Z | m.p.(°C.) |
|---|---|---|---|---|---|---|
| L-6 | H | SO2N(CH3)H | CH3 | OCH2CH3 | N | |
| L-6 | H | SO2CH3 | CH3 | OCH3 | CH | |
| L-6 | H | SO2CH2CH3 | CH3 | CH2CN | N | |
| L-6 | CH3 | SO2CH2CH2CH3 | CH3 | OCH3 | N | |
| L-6 | H | SCH3 | CH3 | CH2CN | N | |
| L-6 | H | S(O)CH3 | H | CH3 | N | |

TABLE 7a

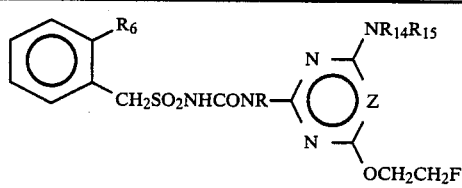

| R | R6 | R14 | R15 | Z | m.p.(°C.) |
|---|---|---|---|---|---|
| CH3 | CO2CH3 | H | CH3 | N | |
| H | CO2CH3 | H | CH3 | CH | |
| H | CO2CH3 | H | CH3 | N | |
| H | CO2CH3 | CH3 | CH3 | CH | |
| H | CO2CH3 | CH2CH3 | CH3 | N | |
| H | CO2CH2CH3 | H | CH3 | CH | |
| H | CO2CH2CH3 | H | CH3 | N | |
| H | CO2CH2CH3 | CH3 | CH3 | N | |
| H | SO2N(CH3)2 | H | CH3 | CH | |
| H | SO2N(CH3)2 | H | CH3 | N | |
| H | SO2N(CH3)2 | CH3 | CH3 | CH | |
| H | SO2N(CH3)2 | CH3 | CH3 | N | |
| H | OSO2CH3 | H | CH3 | N | |
| H | SO2CH3 | H | CH3 | N | |
| H | SO2CH3 | H | CH3 | CH | |
| H | SO2CH2CH2CH3 | H | CH3 | CH | |
| H | SO2CH2CH2CH3 | H | CH3 | N | |
| H | CO2CH3 | CH3 | OCH3 | N | |
| H | CO2CH3 | CH3 | OCH2CH3 | N | |
| H | CO2CH3 | CH3 | CH2CN | N | |
| H | SO2N(CH3)2 | CH3 | OCH3 | N | |
| H | SO2N(CH3)2 | CH3 | CH2CN | N | |
| H | OSO2CH3 | CH3 | OCH3 | CH | |
| H | SO2CH3 | CH3 | OCH3 | CH | |
| H | SO2CH3 | CH3 | CH2CN | N | |
| H | SO2CH2CH3 | CH3 | OCH3 | CH | |
| H | SO2CH2CH3 | CH2CH3 | OCH3 | |  |

TABLE 7b

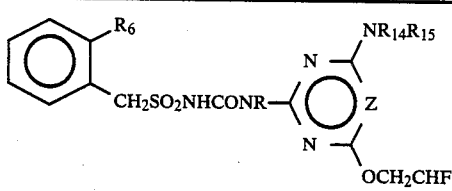

| R | R6 | R14 | R15 | Z | m.p.(°C.) |
|---|---|---|---|---|---|
| CH3 | CO2CH3 | H | CH3 | N | |
| H | CO2CH3 | H | CH3 | CH | |
| H | CO2CH3 | H | CH3 | N | |
| H | CO2CH3 | CH3 | CH3 | CH | |
| H | CO2CH3 | CH2CH3 | CH3 | N | |
| H | CO2CH2CH3 | H | CH3 | CH | |
| H | CO2CH2CH3 | H | CH3 | N | |
| H | CO2CH2CH3 | CH3 | CH3 | N | |

TABLE 7b-continued

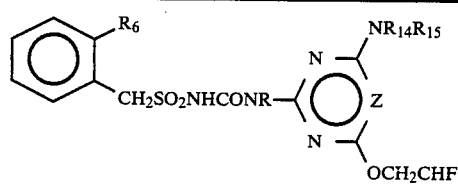

| R | R6 | R14 | R15 | Z | m.p.(°C.) |
|---|---|---|---|---|---|
| H | SO2N(CH3)2 | H | CH3 | CH | |
| H | SO2N(CH3)2 | H | CH3 | N | |
| H | SO2N(CH3)2 | CH3 | CH3 | CH | |
| H | SO2N(CH3)2 | CH3 | CH3 | N | |
| H | OSO2CH3 | H | CH3 | N | |
| H | SO2CH3 | H | CH3 | N | |
| H | SO2CH3 | H | CH3 | CH | |
| H | SO2CH2CH2CH3 | H | CH3 | CH | |
| H | SO2CH2CH2CH3 | H | CH3 | N | |
| CH3 | CO2CH3 | CH3 | OCH3 | CH | |
| H | CO2CH3 | CH3 | OCH3 | N | |
| H | CO2CH3 | CH3 | CH2CN | N | |
| H | CO2CH2CH3 | CH3 | OCH3 | CH | |
| H | SO2N(CH3)2 | CH3 | OCH3 | CH | |
| H | SO2N(CH3)2 | CH3 | CH2CN | N | |
| H | OSO2CH3 | CH3 | OCH2CH3 | N | |
| H | SO2CH3 | CH3 | OCH3 | N | |
| H | SO2CH3 | CH3 | CH2CN | N | |
| H | SO2CH2CH3 | CH3 | OCH3 | N | |

TABLE 7c

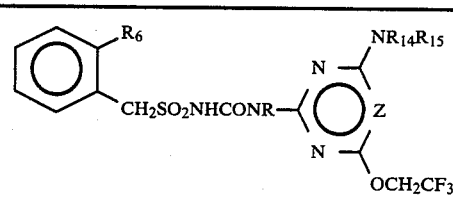

| R | R6 | R14 | R15 | Z | m.p.(°C.) |
|---|---|---|---|---|---|
| CH3 | CO2CH3 | H | CH3 | N | |
| H | CO2CH3 | H | CH3 | CH | |
| H | CO2CH3 | H | CH3 | N | 220–225 |
| H | CO2CH3 | CH3 | CH3 | CH | |
| H | CO2CH3 | CH2CH3 | CH3 | N | |
| H | CO2CH2CH3 | H | CH3 | CH | |
| H | CO2CH2CH3 | H | CH3 | N | |
| H | CO2CH2CH3 | CH3 | CH3 | N | |
| H | SO2N(CH3)2 | H | CH3 | CH | |
| H | SO2N(CH3)2 | H | CH3 | N | |
| H | SO2N(CH3)2 | CH3 | CH3 | CH | |
| H | SO2N(CH3)2 | CH3 | CH3 | N | |
| H | OSO2CH3 | H | CH3 | N | |
| H | SO2CH3 | H | CH3 | N | |
| H | SO2CH3 | H | CH3 | CH | |
| H | SO2CH2CH2CH3 | H | CH3 | CH | |

TABLE 7c-continued

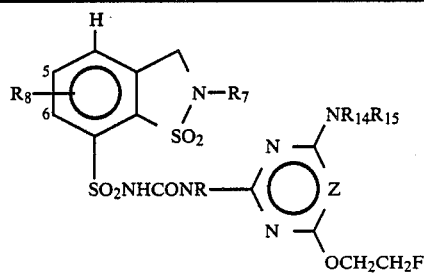

| R | R₆ | R₁₄ | R₁₅ | Z | m.p.(°C.) |
|---|---|---|---|---|---|
| H | SO₂CH₂CH₂CH₃ | H | CH₃ | N | |
| CH₃ | CO₂CH₃ | CH₃ | OCH₃ | CH | |
| H | CO₂CH₃ | CH₃ | OCH₃ | N | |
| H | CO₂CH₃ | CH₃ | CH₂CN | N | |
| H | SO₂N(CH₃)₂ | CH₃ | OCH₃ | N | |
| H | SO₂N(CH₃)₂ | CH₃ | OCH₃ | CH | |
| H | OSO₂CH₃ | CH₃ | OCH₂CH₃ | N | |
| H | SO₂CH₃ | CH₃ | OCH₃ | N | |
| H | SO₂CH₃ | CH₃ | OCH₂CH₃ | N | |
| H | SO₂CH₂CH₃ | CH₃ | OCH₃ | CH | |

TABLE 8a

Structure: benzene ring with H at position, R₈ at 5/6, CH₂-N(R₇)-SO₂ forming fused ring, SO₂NHCONR— connected to pyrimidine/triazine ring with NR₁₄R₁₅, Z, OCH₂CH₂F substituents.

| R | R₇ | R₈ | R₁₄ | R₁₅ | Z | m.p.(°C.) |
|---|---|---|---|---|---|---|
| CH₃ | H | H | H | CH₃ | N | |
| H | H | H | H | CH₃ | CH | |
| H | H | H | H | CH₃ | N | |
| H | H | H | CH₃ | CH₃ | N | |
| H | H | H | CH₃ | CH₃ | CH | |
| H | CH₃ | H | H | CH₃ | N | |
| H | CH₃ | H | H | CH₃ | CH | |
| H | CH₃ | H | CH₃ | CH₃ | N | |
| H | CH₃ | H | CH₃ | CH₃ | CH | |
| H | CH₃ | H | CH₃ | CH₂CH₃ | N | |
| H | CH₂CH₃ | H | H | CH₃ | CH | |
| H | CH₂CH₃ | H | H | CH₃ | N | |
| H | CH₂CH₃ | H | CH₃ | CH₃ | CH | |
| H | CH₂CH₂CH₃ | H | H | CH₃ | N | |
| H | CH₂CH₂CH₃ | H | H | CH₃ | CH | |
| H | CH(CH₃)₂ | H | H | CH₃ | N | |
| H | CH(CH₃)₂ | H | H | CH₃ | CH | |
| H | CH₂CH₂CH₂CH₃ | H | H | CH₃ | CH | |
| H | CH₂CH₂CH₂CH₃ | H | H | CH₃ | N | |
| H | CH₂CH=CH₂ | H | H | CH₃ | CH | |
| H | CH₂CH=CH₂ | H | H | CH₃ | N | |
| H | CH₂CH₂CH=CH₂ | H | H | CH₃ | N | |
| H | CH₂C≡CH | H | H | CH₃ | CH | |
| H | CH₂C≡CH | H | H | CH₃ | N | |
| H | CH₃OCH₂CH₂ | H | H | CH₃ | N | |
| H | CH₂CH₂OCH₂CH₃ | H | H | CH₃ | N | |
| OCH₃ | H | H | H | CH₃ | N | |
| CH₃ | H | H | CH₃ | OCH₃ | N | |
| H | H | H | CH₃ | OCH₃ | N | |
| H | H | H | CH₃ | CH₂CN | N | |
| H | CH₃ | H | CH₃ | OCH₃ | N | |
| H | CH₃ | H | CH₂CH₃ | OCH₃ | N | |
| H | CH₂CH₂CH₃ | H | CH₃ | OCH₃ | N | |
| H | CH₂CH₂CH₃ | H | CH₂CH₃ | OCH₂CH₃ | N | |
| H | CH₂CH₂CH₂CH₃ | H | CH₃ | CH₂CN | N | |
| H | CH₂CH₂CH₂CH₂CH₃ | H | CH₃ | OCH₃ | N | |
| H | CH₂CH=CH₂ | H | CH₃ | OCH₃ | N | |
| H | CH₂CH₂CH=CH₂ | H | CH₃ | OCH₃ | CH | |
| H | CH₂C≡CH | H | CH₂CH₃ | OCH₂CH₃ | N | |
| H | CH₂CH₂OCH₃ | H | CH₃ | OCH₃ | CH | |
| H | CH₂CH₂OCH₃ | H | CH₃ | OCH₃ | N | |
| H | CH₃ | 6-Cl | CH₃ | OCH₂CH₃ | N | |
| H | CH₂CH₂CH₃ | 5-OCH₃ | CH₃ | OCH₃ | CH | |
| H | CH₂CH=CH₂ | 6-Cl | CH₂CH₃ | OCH₂CH₃ | N | |
| CH₃ | CH₂C≡CH | 6-OCH₃ | CH₃ | OCH₃ | CH | |
| H | CH₂CH₂F | H | CH₃ | CH₃ | N | |
| H | CH₂CH₂CH₂F | H | H | CH₃ | CH | |

TABLE 8b

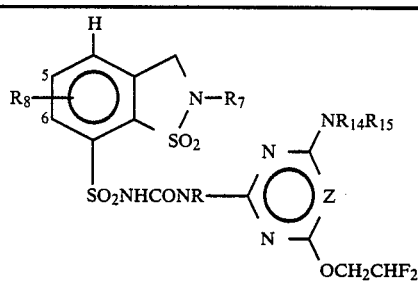

| R | R7 | R8 | R14 | R15 | Z | m.p.(°C.) |
|---|---|---|---|---|---|---|
| CH3 | H | H | H | CH3 | N | |
| H | H | H | H | CH3 | CH | |
| H | H | H | H | CH3 | N | |
| H | H | H | CH3 | CH3 | N | |
| H | H | H | CH3 | CH3 | CH | |
| H | CH3 | H | H | CH3 | N | |
| H | CH3 | H | H | CH3 | CH | |
| H | CH3 | H | CH3 | CH3 | N | |
| H | CH3 | H | CH3 | CH3 | CH | |
| H | CH3 | H | CH3 | CH2CH3 | N | |
| H | CH2CH3 | H | H | CH3 | CH | |
| H | CH2CH3 | H | H | CH3 | N | |
| H | CH2CH3 | H | CH3 | CH3 | CH | |
| H | CH2CH2CH3 | H | H | CH3 | N | |
| H | CH2CH2CH3 | H | H | CH3 | CH | |
| H | CH(CH3)2 | H | H | CH3 | N | |
| H | CH(CH3)2 | H | H | CH3 | CH | |
| H | CH2CH2CH2CH3 | H | H | CH3 | CH | |
| H | CH2CH2CH2CH3 | H | H | CH3 | N | |
| H | CH2CH=CH2 | H | H | CH3 | CH | |
| H | CH2CH=CH2 | H | H | CH3 | N | |
| H | CH2CH2CH=CH2 | H | H | CH3 | N | |
| H | CH2C≡CH | H | H | CH3 | CH | |
| H | CH2C≡CH | H | H | CH3 | N | |
| H | H | 6-Cl | H | CH3 | N | |
| CH3 | H | H | CH3 | OCH3 | N | |
| H | H | H | CH3 | OCH3 | N | |
| H | H | H | CH3 | CH2CN | N | |
| H | CH3 | H | CH3 | OCH3 | N | |
| H | CH3 | H | CH2CH3 | OCH3 | N | |
| H | CH2(CH3)2 | H | CH3 | OCH3 | CH | |
| H | CH2CH2CH3 | H | CH2CH3 | OCH2CH3 | N | |
| H | CH2CH2CH2CH3 | H | CH3 | OCH3 | CH | |
| H | CH2CH2CH2CH3 | H | H | OCH3 | N | |
| H | CH2CH2CH2CH2CH3 | H | CH3 | OCH3 | N | |
| H | CH2CH2CH=CH2 | H | CH3 | OCH3 | N | |
| H | CH2CH2CH=CH2 | H | CH3 | OCH3 | CH | |
| H | CH2C≡CH | H | CH3 | OCH3 | N | |
| H | CH2CH2OCH3 | H | CH3 | OCH3 | CH | |
| H | CH3 | 6-Cl | CH3 | OCH2CH3 | N | |
| H | CH2CH2CH3 | 5-OCH3 | CH3 | OCH3 | CH | |
| H | CH2CH=CH2 | 6-Cl | CH2CH3 | OCH2CH3 | N | |
| H | CH2C≡CH | 6-OCH3 | CH3 | OCH2CH3 | N | |
| H | CH2CH2F | H | H | CH3 | N | |
| H | CH2CH2CH2F | H | H | CH3 | CH | |

TABLE 8c

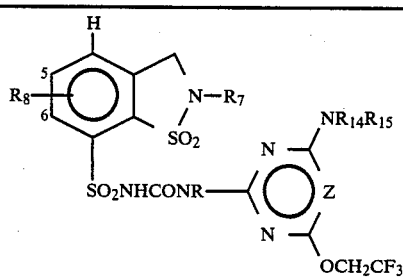

| R | R7 | R8 | R14 | R15 | Z | m.p.(°C.) |
|---|---|---|---|---|---|---|
| CH3 | H | H | H | CH3 | N | |
| H | H | H | H | CH3 | CH | |
| H | H | H | H | CH3 | N | |

TABLE 8c-continued

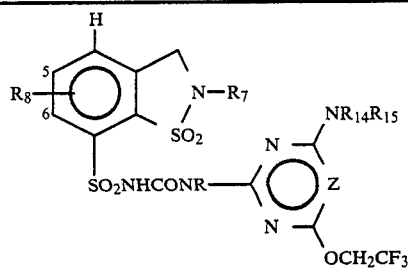

| R | R7 | R8 | R14 | R15 | Z | m.p.(°C.) |
|---|---|---|---|---|---|---|
| H | H | H | CH3 | CH3 | N | |
| H | H | H | CH3 | CH3 | CH | |
| H | CH3 | H | H | CH3 | N | |
| H | CH3 | H | H | CH3 | CH | |
| H | CH3 | H | CH3 | CH3 | N | |
| H | CH3 | H | CH3 | CH3 | CH | |
| H | CH3 | H | CH3 | CH2CH3 | N | |
| H | CH2CH3 | H | H | CH3 | CH | |
| H | CH2CH3 | H | H | CH3 | N | |
| H | CH2CH3 | H | CH3 | CH3 | CH | |
| H | CH2CH2CH3 | H | H | CH3 | N | |
| H | CH2CH2CH3 | H | H | CH3 | CH | |
| H | CH(CH3)2 | H | H | CH3 | N | |
| H | CH(CH3)2 | H | H | CH3 | CH | |
| H | CH2CH2CH2CH3 | H | H | CH3 | CH | |
| H | CH2CH2CH2CH3 | H | H | CH3 | N | |
| H | CH2CH=CH2 | H | H | CH3 | CH | |
| H | CH2CH=CH2 | H | H | CH3 | N | |
| H | CH2CH2CH=CH2 | H | H | CH3 | N | |
| H | CH2C≡CH | H | H | CH3 | CH | |
| H | CH2C≡CH | H | H | CH3 | N | |
| H | CH2CH2OCH3 | H | H | CH3 | N | |
| CH3 | H | H | CH3 | OCH3 | N | |
| H | H | H | CH3 | OCH3 | N | |
| H | H | H | CH3 | OCH2CH3 | N | |
| H | CH3 | H | CH3 | OCH3 | N | |
| H | CH3 | H | CH3 | OCH3 | CH | |
| H | CH2(CH3)2 | H | CH3 | OCH3 | CH | |
| H | CH2CH2CH3 | H | CH3 | OCH3 | N | |
| H | CH2CH2CH3 | H | CH2CH3 | OCH2CH3 | N | |
| H | CH2CH2CH2CH3 | H | CH3 | CH2CN | N | |
| H | CH2CH=CH2 | H | CH3 | OCH3 | N | |
| H | CH2CH2C≡CH | H | CH3 | OCH3 | CH | |
| H | CH2C≡CH | H | CH3 | OCH3 | N | |
| H | CH2CH2OCH3 | H | CH3 | OCH3 | CH | |
| H | CH2CH2OCH2CH3 | H | CH3 | OCH3 | N | |
| H | CH3 | 6-Cl | CH3 | OCH2CH3 | N | |
| H | CH2CH=CH2 | 6-Cl | CH2CH3 | OCH2CH3 | N | |
| CH3 | CH2C≡CH | 6-OCH3 | CH3 | OCH3 | CH | |
| H | CH2C≡CH | 6-Cl | CH3 | CH2CN | N | |
| H | CH2CH2F | H | H | CH3 | N | |
| H | CH2CH2CH2F | H | H | CH2CH3 | CH | |

TABLE 9a

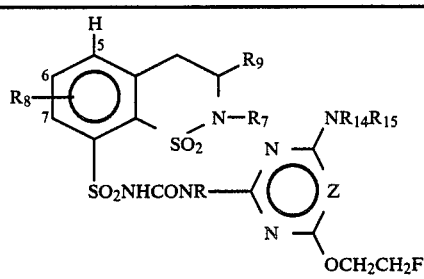

| R | R7 | R8 | R9 | R14 | R15 | Z | m.p.(°C.) |
|---|---|---|---|---|---|---|---|
| CH3 | CH3 | H | H | H | CH3 | N | |
| H | H | H | H | H | CH3 | N | |
| H | H | H | H | H | CH3 | CH | |
| H | H | H | H | CH3 | CH3 | N | |
| H | H | H | H | CH3 | CH3 | CH | |
| H | H | H | H | CH3 | CH3 | CH | |

TABLE 9a-continued

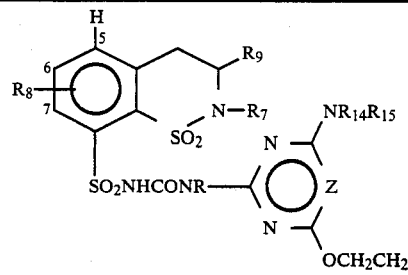

| R | R7 | R8 | R9 | R14 | R15 | Z | m.p.(°C.) |
|---|---|---|---|---|---|---|---|
| H | CH2CH3 | H | H | H | CH3 | CH | |
| H | CH2CH3 | H | H | H | CH3 | N | |
| H | CH2CH3 | H | H | CH3 | CH3 | N | |
| H | CH2CH3 | H | H | CH2CH3 | CH3 | N | |
| H | CH2CH3 | H | CH3 | H | CH3 | N | |
| H | CH(CH3)2 | H | H | H | CH3 | CH | |
| H | CH(CH3)2 | H | H | H | CH3 | N | |
| H | CH2CH2CH3 | H | H | H | CH3 | N | |
| H | CH2CH2CH3 | H | H | H | CH3 | CH | |
| H | CH2CH2CH3 | H | H | CH3 | CH3 | CH | |
| H | CH2CH2CH2CH3 | H | H | H | CH3 | CH | |
| H | CH2CH2CH2CH3 | H | H | H | CH3 | N | |
| H | CH2CH2CH2CH3 | H | CH3 | H | CH3 | N | |
| H | CH2CH2CH2CH2CH3 | H | H | H | CH3 | N | |
| H | CH2CH2CH2CH2CH3 | H | H | H | CH3 | CH | |
| H | CH2CH2CH2CH2CH3 | H | CH3 | H | CH3 | CH | |
| H | CH2CH2CH2CH2CH3 | H | CH3 | H | CH3 | N | |
| H | CH2CH2CH2CH2CH3 | H | CH3 | CH3 | CH3 | CH | |
| H | CH—CH=CH2 | H | H | H | CH3 | N | |
| H | CH—C≡CH | H | H | H | CH3 | N | |
| H | CH2CH2—OCH3 | H | H | H | CH3 | N | |
| H | CH2CH2—OCH2CH3 | H | H | H | CH3 | N | |
| H | CH3 | H | H | CH3 | CH2CN | N | |
| H | H | H | H | CH3 | OCH3 | N | |
| H | CH3 | H | CH3 | CH3 | OCH3 | N | |
| H | CH3 | H | H | CH3 | OCH3 | N | |
| H | CH3 | H | H | CH2CH3 | OCH2CH3 | N | |
| H | CH2CH3 | H | H | CH3 | OCH3 | N | |
| H | CH(CH3)2 | H | H | CH3 | OCH3 | CH | |
| H | CH2CH2CH3 | H | CH3 | CH3 | OCH3 | N | |
| H | CH2CH2CH3 | H | CH3 | CH2CH3 | OCH3 | N | |
| H | CH2CH2CH2CH3 | H | CH3 | CH3 | OCH3 | N | |
| H | CH2CH2CH2CH3 | H | CH3 | CH3 | CH2CN | N | |
| H | CH2CH2CH2CH2CH3 | H | CH3 | CH3 | CH2CN | N | |
| H | CH2CH=CH2 | H | H | CH3 | OCH3 | N | |
| H | CH2C≡CH | H | H | CH3 | OCH3 | CH | |
| H | CH2CH2OCH3 | H | H | CH3 | OCH2CH3 | N | |
| H | CH3 | 6-CH3 | H | CH3 | OCH3 | N | |
| H | CH3 | 7-CH3 | CH3 | CH3 | OCH3 | CH | |
| H | CH2CH2CH3 | 7-Cl | CH3 | CH3 | OCH3 | CH | |
| H | CH2CH=CH2 | 6-OCH3 | H | CH3 | OCH3 | CH | |
| H | CH2CH=CH2 | 7-Cl | CH3 | CH3 | OCH3 | N | |

TABLE 9b

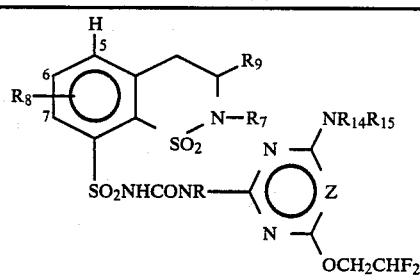

| R | R7 | R8 | R9 | R14 | R15 | Z | m.p.(°C.) |
|---|---|---|---|---|---|---|---|
| CH3 | CH3 | H | H | H | CH3 | N | |
| H | H | H | H | H | CH3 | N | |
| H | H | H | H | H | CH3 | CH | |
| H | H | H | H | CH3 | CH3 | N | |
| H | H | H | CH3 | H | CH3 | CH | |
| H | H | H | CH3 | CH3 | CH3 | CH | |

TABLE 9b-continued

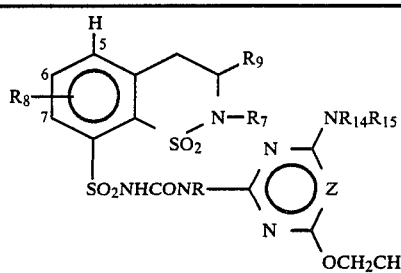

| R | R$_7$ | R$_8$ | R$_9$ | R$_{14}$ | R$_{15}$ | Z | m.p.(°C.) |
|---|---|---|---|---|---|---|---|
| H | CH$_2$CH$_3$ | H | H | H | CH$_3$ | CH | |
| H | CH$_2$CH$_3$ | H | H | H | CH$_3$ | N | |
| H | CH$_2$CH$_3$ | H | H | CH$_3$ | CH$_3$ | N | |
| H | CH$_2$CH$_3$ | H | H | CH$_2$CH$_3$ | CH$_3$ | N | |
| H | CH$_2$CH$_3$ | H | CH$_3$ | H | CH$_3$ | N | |
| H | CH(CH$_3$)$_2$ | H | H | H | CH$_3$ | CH | |
| H | CH(CH$_3$)$_2$ | H | H | H | CH$_3$ | N | |
| H | CH$_2$CH$_2$CH$_3$ | H | H | H | CH$_3$ | N | |
| H | CH$_2$CH$_2$CH$_3$ | H | H | H | CH$_3$ | CH | |
| H | CH$_2$CH$_2$CH$_3$ | H | CH$_3$ | CH$_3$ | CH$_3$ | CH | |
| H | CH$_2$CH$_2$CH$_2$CH$_3$ | H | H | H | CH$_3$ | CH | |
| H | CH$_2$CH$_2$CH$_2$CH$_3$ | H | H | H | CH$_3$ | N | |
| H | CH$_2$CH$_2$CH$_2$CH$_3$ | H | H | H | CH$_3$ | N | |
| H | CH$_2$CH$_2$CH$_2$CH$_2$CH$_3$ | H | H | H | CH$_3$ | N | |
| H | CH$_2$CH$_2$CH$_2$CH$_2$CH$_3$ | H | H | H | CH$_3$ | CH | |
| H | CH$_2$CH$_2$CH$_2$CH$_2$CH$_3$ | H | CH$_3$ | H | CH$_3$ | CH | |
| H | CH$_2$CH$_2$CH$_2$CH$_2$CH$_3$ | H | CH$_3$ | H | CH$_3$ | N | |
| H | CH$_2$CH$_2$CH$_2$CH$_2$CH$_3$ | H | CH$_3$ | CH$_3$ | CH$_3$ | CH | |
| H | CH$_3$ | 6-OCH$_3$ | H | H | CH$_3$ | N | |
| CH$_3$ | CH$_3$ | H | H | CH$_3$ | OCH$_3$ | N | |
| H | H | H | H | H | OCH$_3$ | N | |
| H | CH$_3$ | H | CH$_3$ | CH$_3$ | OCH$_3$ | N | |
| H | CH$_3$ | H | H | CH$_3$ | OCH$_3$ | N | |
| H | CH$_3$ | H | H | CH$_2$CH$_3$ | OCH$_2$CH$_3$ | N | |
| H | CH$_2$CH$_3$ | H | H | CH$_3$ | OCH$_3$ | N | |
| H | CH$_2$CH$_3$ | H | H | CH$_3$ | CH$_2$CN | N | |
| H | CH(CH$_3$)$_2$ | H | H | CH$_3$ | OCH$_3$ | CH | |
| H | CH$_2$CH$_2$CH$_3$ | H | CH$_3$ | CH$_3$ | OCH$_3$ | N | |
| H | CH$_2$CH$_2$CH$_3$ | H | CH$_3$ | CH$_2$CH$_3$ | OCH$_3$ | N | |
| H | CH$_2$CH$_2$CH$_2$CH$_3$ | H | CH$_3$ | CH$_3$ | OCH$_3$ | N | |
| H | CH$_2$CH=CH$_2$ | H | H | CH$_3$ | OCH$_3$ | CH | |
| H | CH$_2$C≡CH | H | H | CH$_3$ | OCH$_3$ | CH | |
| H | CH$_2$CH$_2$C≡CH | H | CH$_3$ | CH$_3$ | OCH$_3$ | N | |
| H | CH$_2$CH$_2$OCH$_3$ | H | H | CH$_3$ | OCH$_2$CH$_3$ | N | |
| H | CH$_3$ | 6-CH$_3$ | H | CH$_3$ | OCH$_3$ | N | |
| H | CH$_3$ | 7-CH$_3$ | H | CH$_3$ | OCH$_2$CH$_3$ | N | |
| H | CH$_2$CH$_2$CH$_3$ | 7-Cl | CH$_3$ | CH$_3$ | OCH$_3$ | CH | |
| H | CH$_2$CH$_2$CH$_2$ | 6-OCH$_3$ | H | CH$_3$ | OCH$_3$ | N | |
| H | CH$_2$CH=CH$_2$ | 7-Cl | CH$_3$ | CH$_3$ | OCH$_3$ | N | |

TABLE 9c

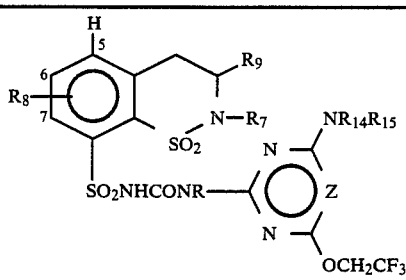

| R | R$_7$ | R$_8$ | R$_9$ | R$_{14}$ | R$_{15}$ | Z | m.p.(°C.) |
|---|---|---|---|---|---|---|---|
| CH$_3$ | CH$_3$ | H | H | H | CH$_3$ | N | |
| H | H | H | H | H | CH$_3$ | N | |
| H | H | H | H | H | CH$_3$ | CH | |
| H | H | H | H | CH$_3$ | CH$_3$ | N | |
| H | H | H | CH$_3$ | H | CH$_3$ | CH | |
| H | H | H | CH$_3$ | CH$_3$ | CH$_3$ | CH | |
| H | CH$_2$CH$_3$ | H | H | H | CH$_3$ | CH | |
| H | CH$_2$CH$_3$ | H | H | H | CH$_3$ | N | |
| H | CH$_2$CH$_3$ | H | H | CH$_3$ | CH$_3$ | N | |

TABLE 9c-continued

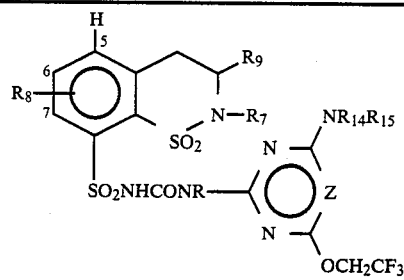

| R | R7 | R8 | R9 | R14 | R15 | Z | m.p.(°C.) |
|---|---|---|---|---|---|---|---|
| H | CH2CH3 | H | H | CH2CH3 | CH3 | N | |
| H | CH2CH3 | H | CH3 | H | CH3 | N | |
| H | CH(CH3)2 | H | H | H | CH3 | CH | |
| H | CH(CH3)2 | H | H | H | CH3 | N | |
| H | CH2CH2CH3 | H | H | H | CH3 | N | |
| H | CH2CH2CH3 | H | H | H | CH3 | CH | |
| H | CH2CH2CH3 | H | H | CH3 | CH3 | CH | |
| H | CH2CH2CH2CH3 | H | H | H | CH3 | CH | |
| H | CH2CH2CH2CH3 | H | H | H | CH3 | N | |
| H | CH2CH2CH2CH3 | H | CH3 | H | CH3 | N | |
| H | CH2CH2CH2CH2CH3 | H | H | H | CH3 | N | |
| H | CH2CH2CH2CH2CH3 | H | H | H | CH3 | CH | |
| H | CH2CH2CH2CH2CH3 | H | CH3 | H | CH3 | CH | |
| H | CH2CH2CH2CH2CH3 | H | CH3 | H | CH3 | N | |
| H | CH2CH2CH2CH2CH3 | H | CH3 | CH3 | CH3 | CH | |
| CH3 | CH3 | H | H | H | OCH3 | N | |
| H | CH3 | H | H | H | CH2CN | N | |
| H | H | H | H | CH3 | OCH3 | CH | |
| H | CH3 | H | CH3 | CH3 | OCH3 | N | |
| H | CH3 | H | H | CH3 | OCH3 | CH | |
| H | CH3 | H | H | CH2CH3 | OCH2CH3 | N | |
| H | CH2CH3 | H | H | CH3 | OCH3 | CH | |
| H | CH2CH3 | H | H | CH3 | CH2CN | N | |
| H | CH2CH2CH3 | H | H | CH3 | OCH3 | N | |
| H | CH2CH2CH3 | H | CH3 | CH3 | OCH3 | N | |
| H | CH2CH2CH3 | H | CH3 | H | OCH3 | N | |
| H | CH2CH2CH2CH3 | H | H | CH3 | OCH3 | CH | |
| H | CH2CH2CH2CH3 | H | CH3 | CH3 | CH2CN | N | |
| H | CH2CH=CH2 | H | H | CH3 | OCH3 | CH | |
| H | CH2C≡CH | H | H | CH3 | OCH3 | CH | |
| H | CH2C≡CH | H | H | CH3 | OCH3 | N | |
| H | CH2CH2OCH3 | H | H | CH3 | OCH3 | N | |
| H | CH2CH2OCH3 | H | H | CH3 | OCH2CH3 | N | |
| H | CH2CH2OCH2CH3 | H | H | CH2CH3 | OCH2CH3 | N | |
| H | CH3 | 6-CH3 | H | CH3 | OCH3 | N | |
| H | CH3 | 7-CH3 | H | CH3 | OCH2CH3 | N | |
| H | CH2CH2CH3 | 7-Cl | CH3 | CH3 | OCH3 | CH | |
| H | CH2CH=CH2 | 7-Cl | H | CH3 | OCH2CH3 | N | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 10

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 4

Wettable Powder

| | |
|---|---|
| 2-[[[4-(methylamino)-6-(2,2,2-trifluoroethoxy)-1,3,5-triazin-2-yl]aminocarbonyl]aminosulfonyl]benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 5

Wettable Powder

| | |
|---|---|
| 2-[[[4-(methylamino)-6-(2,2,2-trifluoroethoxy)-1,3,5-triazin-2-yl]aminocarbonyl]aminosulfonyl]benzoic acid, ethyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 6

Granule

| | |
|---|---|
| Wettable Powder of Example 4 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 7

Extruded Pellet

| | |
|---|---|
| 2-[[[4-(methylamino)-6-(2,2,2-trifluoroethoxy)-1,3,5-triazin-2-yl]aminocarbonyl]aminosulfonyl]benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

Oil Suspension

| | |
|---|---|
| 2-[[[4-(methylamino)-6-(2,2,2-trifluoroethoxy)-1,3,5-triazin-2-yl]aminocarbonyl]aminosulfonyl]benzoic acid, ethyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

Wettable Powder

| | |
|---|---|
| 2-[[[4-(methylamino)-6-(2,2,2-trifluoroethoxy)-1,3,5-triazin-2-yl]aminocarbonyl]aminosulfonyl]benzoic acid, methyl ester | 20% |
| sodium alkylnaphthalenesulfonate | 4% |
| sodium ligninsulfonate | 4% |

| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 10

Low Strength Granule

| 2-[[[4-(methylamino)-6-(2,2,2-trifluoroethoxy)-1,3,5-triazin-2-yl]aminocarbonyl]aminosulfonyl]benzoic acid, ethyl ester | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After sparying of the solution has been completed, the blender is allowed to run for a short period and then the granules are packaged.

EXAMPLE 11

Aqueous Suspension

| 2-[[[4-(methylamino)-6-(2,2,2-trifluoroethoxy)-1,3,5-triazin-2-yl]aminocarbonyl]aminosulfonyl]benzoic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 12

Solution

| 2-[[[4-(methylamino)-6-(2,2,2-trifluoroethoxy)-1,3,5-triazin-2-yl]aminocarbonyl]aminosulfonyl]benzoic acid, ethyl ester, sodium salt | 5% |
| water | 95% |

The salt is added directly to the water with stirring to produce the solution, which may then be packaged for use.

EXAMPLE 13

Low Strength Granule

| 2-[[[4-(methylamino)-6-(2,2,2-trifluoroethoxy)-1,3,5-triazin-2-yl]aminocarbonyl]aminosulfonyl]benzoic acid, methyl ester | 0.1% |
| attapulgite granules (U.S.S. 20-40 mesh) | 99.9% |

The active ingredient is dissolved in a solvent and the solution is sprayed upon dedusted graules in a double-cone blender. After spraying of the solution has been completed, the material is warmed to evaporate the solvent. The material is allowed to cool and then packaged.

EXAMPLE 14

Granule

| 2-[[[4-(methylamino)-6-(2,2,2-trifluoroethoxy)-1,3,5-triazin-2-yl]aminocarbonyl]aminosulfonyl]benzoic acid, ethyl ester | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The sparying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 15

High Strength Concentrate

| 2-[[[4-(methylamino)-6-(2,2,2-trifluoroethoxy)-1,3,5-triazin-2-yl]aminocarbonyl]aminosulfonyl]benzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 16

Wettable Powder

| 2-[[[4-(methylamino)-6-(2,2,2-trifluoroethoxy)-1,3,5-triazin-2-yl]aminocarbonyl]aminosulfonyl]benzoic acid, ethyl ester | 90% |
| dioctyl sodium sulfosuccinate | 0.1% |
| synthetic fine silica | 9.9% |

The ingredients are blended and ground in a hammer mill to produce particles essentially all below 100 microns. The material is sifted through a U.S.S. No. 50 screen and then packaged.

EXAMPLE 17

Wettable Powder

| 2-[[[4-(methylamino)-6-(2,2,2-trifluoroethoxy)-1,3,5-triazin-2-yl]aminocarbonyl]aminosulfonyl]benzoic acid, ethyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 18

Oil Suspension

| | |
|---|---|
| 2-[[[4-(methylamino)-6-(2,2,2-trifluoroethoxy)-1,3,5-triazin-2-yl]aminocarbonyl]aminosulfonyl]benzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 19

Dust

| | |
|---|---|
| 2-[[[4-(methylamino)-6-(2,2,2-trifluoroethoxy)-1,3,5-triazin-2-yl]aminocarbonyl]aminosulfonyl]benzoic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 20

Emulsifiable Concentrate

| | |
|---|---|
| 2-[[[4-(methylamino)-6-(2,2,2-trifluoroethoxy)-1,3,5-triazin-2-yl]aminocarbonyl]aminosulfonyl]benzoic acid, ethyl ester | 10% |
| chlorobenzene | 84% |
| sorbitan monostearate and polyoxyethylene condensates thereof | 6% |

The ingredients are combined and stirred to produce a solution which can be emulsified in water for application.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

Compounds

Compound 1 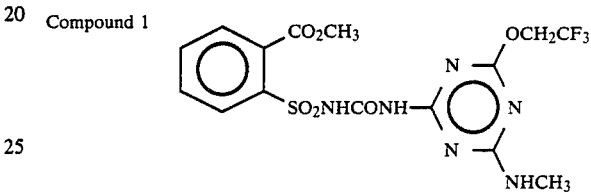

Compound 2 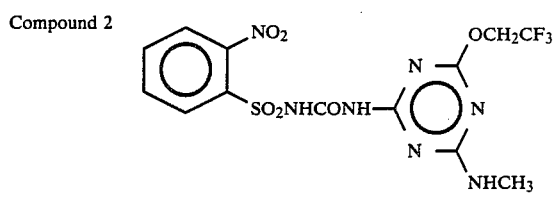

Compound 3 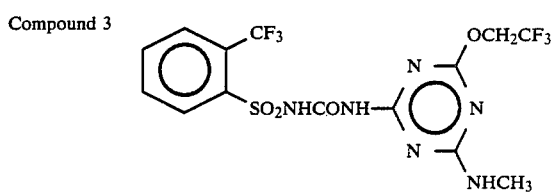

Compound 4 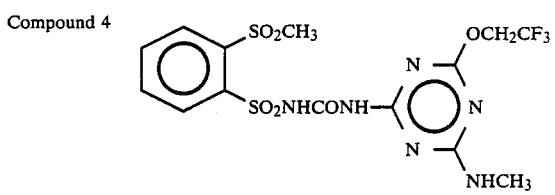

Compound 5 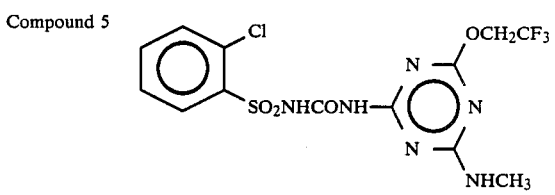

Compound 6 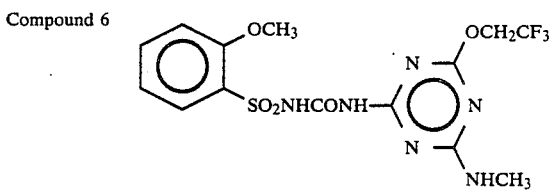

-continued
Compounds

Compound 7 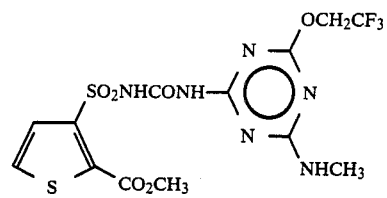

Compound 8 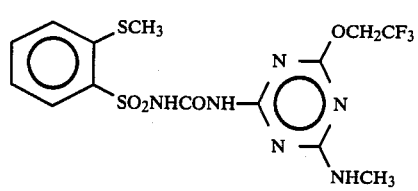

Compound 9 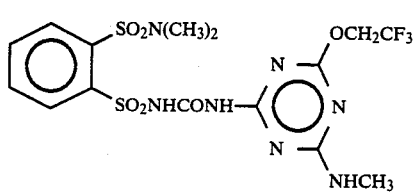

Compound 10 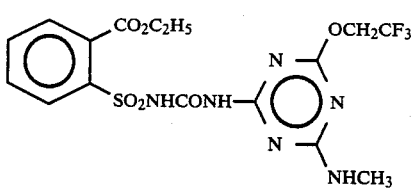

Compound 11 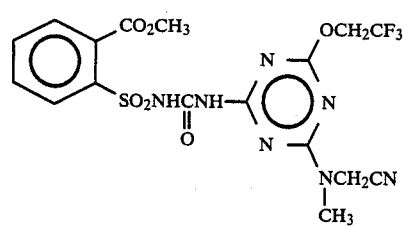

-continued
Compounds

Compound 12 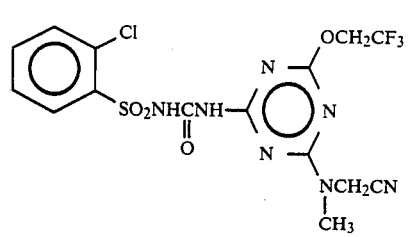

TEST A

Seeds of crabgrass (*Digitaria spp.*), barnyardgrass (*Echinochloa crusgalli*), wild oats (*Avena fatua*), sicklepod (*Cassia obtusifolia*), morningglory (*Ipomoea spp.*), cocklebur (*Xanthium pensylvanicum*), sorghum, corn, soybean, sugar beet, cotton, rice, wheat and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

B=burn;
C=chlorosis/necrosis;
D=defoliation;
E=emergence inhibition;
G=growth retardation;
H=formative effect;
U=unusual pigmentation;
X=axillary stimulation;
S=albinism; and
6Y=abscised buds of flowers.

TABLE A

| Rate kg/ha | Cmpd. 1 0.05 | Cmpd. 2 0.05 | Cmpd. 3 0.05 | Cmpd. 4 0.05 | Cmpd. 5 0.05 | Cmpd. 6 0.05 | Cmpd. 7 0.05 | Cmpd. 8 0.05 | Cmpd. 9 0.05 | Cmpd. 10 0.05 | Cmpd. 11 0.1 | Cmpd. 12 0.1 |
|---|---|---|---|---|---|---|---|---|---|---|---|---|
| POST-EMERGENCE |
| Morningglory | 10C | 6C,9G | 9C | 10C | 10C | 10C | 4C,9G | 2C,6H | 10C | 9C | 4C,9G | 4C,9G |
| Cocklebur | 9C | 6C,9G | 10C | 5C,9G | 9C | 2C,9G | 5C,9G | 2C,8H | 5C,9G | 9C | 5C,9G | 2C,8G |
| Sicklepod | 5C,9G | 4C,8G | 9C | 5C,9G | 5C,9G | 5C,9G | 3C,5G | 4C,9G | 5C,9G | 5C,9G | — | — |
| Nutsedge | 2C,8G | 2C,5G | 4G | 4G | 0 | 0 | 5G | 4G | 5G | 9G | 5C,9G | 3G |
| Crabgrass | 2C,6G | 3C,8G | 5G | 2C,5G | 0 | 3G | 2G | 0 | 8G | 2G | 3C,7G | 0 |
| Barnyardgrass | 5C,9H | 5C,9H | 3C,5G | 3C,9H | 3C,4H | 3C,9H | 2C | 2C,3H | 2C,9H | 3C,8H | 3C,9H | 3C,6H |
| Wild Oats | 5C,9G | 5C,9G | 3C,8G | 3C,9G | 0 | 3C,8H | 3G | 2C,5G | 4C,9G | 5C,9G | 2C,9G | 0 |
| Wheat | 7G | 8G | 0 | 2C,8G | 0 | 0 | 3G | 0 | 2C,8G | 2G | 2C,9G | 0 |
| Corn | 9G | 9G | 5C,9G | 4C,9H | 3C,8H | 9G | 0 | 3C,9H | 3C,9H | 3C,9H | 9G | 2C,7H |
| Soybean | 5C,9G | 5C,9H | 5C,9H | 3C,5H | 3C,8H | 4C,9G | 0 | 3C,6H | 4C,8H | 5C,9H | 3C,9G | 9G |
| Rice | 9C | 5C,9G | 5C,9G | 5C,9G | 3C,8G | 5C,9G | 6G | 5G | 5C,9G | 6C,9G | 9C | 8G |
| Sorghum | 5C,9H | 4C,9G | 6C,9H | 4C,8H | 3C,5H | 3C,9H | 2C,5H | 2C,5G | 3C,8H | 3C,9H | 2C,9H | 4G |
| Sugar beet | 9C | 9C | 9C | 9C | 9C | 9C | 10C | 5C,9G | 9C | 9C | 10C | 9C |
| Cotton | 4C,9G | 2C,8H | 3C,8H | 3C,7H | 0 | 2C,9G | 2C,8H | 4C,9H | 4C,9G | 5C,9H | 3C,9G | 3C,6H |
| Cheatgrass | | | | | | | | | — | — | 2C,6G | 0 |
| Velvetleaf | | | | | | | | | — | — | 9C | 3C,8H |
| PRE-EMERGENCE |
| Morningglory | 9G | 9G | 9G | 9G | 9G | 9G | 9G | 8G | 2C,9G | 9G | 9G | 8G |
| Cocklebur | 9H | 8H | 9H | 8H | 2C | 8H | 8H | 5G | 7H | 9H | — | — |
| Sicklepod | 4C,9G | 8G | 5C,9G | 3C | 4C,9G | 9C | 0 | 3C,9G | 4C,9G | 4C,8G | — | — |
| Nutsedge | 10E | 5G | 9G | 3C,7G | 3G | 8G | 0 | 5G | 2G | 10E | 9G | 0 |
| Crabgrass | 2C,8G | 2G | 5G | 2G | 0 | 5G | 0 | 0 | 2C,5G | 2G | 2C | 0 |
| Barnyardgrass | 3C,9H | 3C,9H | 6G | 3C,9H | 5G | 3C,9H | 2G | 3C,7H | 3C,9H | 8G | 3C,9H | 3G |

TABLE A-continued

| Rate kg/ha | Cmpd. 1 0.05 | Cmpd. 2 0.05 | Cmpd. 3 0.05 | Cmpd. 4 0.05 | Cmpd. 5 0.05 | Cmpd. 6 0.05 | Cmpd. 7 0.05 | Cmpd. 8 0.05 | Cmpd. 9 0.05 | Cmpd. 10 0.05 | Cmpd. 11 0.1 | Cmpd. 12 0.1 |
|---|---|---|---|---|---|---|---|---|---|---|---|---|
| Wild Oats | 5C,9H | 5C,9H | 2C,9G | 3C,8G | 2C,6G | 3C,8G | 2C,5G | 2C,5G | 3C,8G | 4C,9G | 7C,9G | 0 |
| Wheat | 3C,9H | 5C,9H | 6G | 2C,9G | 3G | 6G | 6G | 3G | 2C,9G | 5G | 9H | 0 |
| Corn | 2C,9G | 5C,9H | 2C,9G | 9G | 2C,9G | 3C,9G | 2C,5G | 3C,7G | 3C,9G | 4C,9G | 3C,9H | 2C,8G |
| Soybean | 9H | 9H | 9H | 2C,2H | 3C,8H | 3C,8H | 1H | 2C,2H | 3C,5G | 9H | 3C,6G | 4C,4H |
| Rice | 10E | 10E | 10E | 5C,9H | 3C,8G | 9H | 7G | 4C,8H | 9H | 10E | 10E | 3C,5G |
| Sorghum | 5C,9H | 5C,9H | 5C,9H | 4C,9G | 2C,4G | 4C,9H | 2C,8G | 4C,9H | 3C,8H | 4C,9H | 4C,9H | 3C,5G |
| Sugar beet | 5C,9G | 5C,9G | 5C,9G | 4C,8G | 4C,9G | 4C,8G | 5C,9G | 4C,9G | 4C,9G | 5C,9G | 9C | 9C |
| Cotton | 8G | 2C,7G | 8G | 2C | 3G | 5G | 2G | 0 | 2C,5G | 7G | 2C,7H | 0 |
| Cheatgrass | | | | | | | — | — | | | 10H | 5G |
| Velvetleaf | | | | | | | — | — | | | 3C,8H | 4G |

TEST B

Postemergence

Two round pans (25 cm diameter by 12.5 cm deep) were filled with Woodstown sandy loam soil. One pan was planted with blackgrass (*Alopecurus myosuroides*), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xantium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed postemergence with the chemicals dissolved in a non-phytotoxic solvent.

Preemergence

Two round pans (25 cm diameter by 12.5 cm deep) were filled with Woodstown sandy loam soil. One pan was planted with blackgrass (*Alopecurus myosuroides*), sugar beets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response.

Response ratings are based on a scale of 0 to 100: where 0=no effect, and 100=complete control. A dash (-) response means no test.

Response ratings are contained in Table B.

TABLE B

| | Compound 1 | | | Compound 2 | | | Compound 3 | | | Compound 4 | | Compound 5 | |
|---|---|---|---|---|---|---|---|---|---|---|---|---|---|
| POSTEMERGENCE | | | | | | | | | | | | | |
| Rate g/ha | 62 | 16 | 4 | 62 | 16 | 4 | 62 | 16 | 4 | 62 | 16 | 62 | 16 |
| Corn | 100 | 70 | 40 | 100 | 80 | 20 | 100 | 90 | 30 | 80 | 20 | 50 | 30 |
| Wheat | 0 | 0 | 0 | 0 | 0 | 0 | 0 | 0 | 0 | 0 | 0 | 0 | 0 |
| Rice | 100 | 90 | 70 | 90 | 80 | 30 | 100 | 90 | 50 | 90 | 60 | 30 | 0 |
| Soybean | 90 | 80 | 20 | 90 | 90 | 50 | 90 | 90 | 70 | 80 | 50 | 90 | 70 |
| Cotton | 90 | 70 | 20 | 30 | 0 | 0 | 20 | 0 | 0 | 70 | 20 | 20 | 0 |
| Sugar beet | 100 | 90 | 80 | 90 | 90 | 50 | 100 | 90 | 50 | 80 | 50 | 100 | 80 |
| Rape | 20 | 0 | 0 | 0 | 0 | 0 | 20 | 0 | 0 | 20 | 0 | 0 | 0 |
| Crabgrass | 40 | 20 | 0 | 0 | 0 | 0 | 50 | 0 | 0 | 0 | 0 | 0 | 0 |
| Johnsongrass | 60 | 20 | 0 | 90 | 40 | 0 | 90 | 80 | 20 | 40 | 0 | 0 | 0 |
| Blackgrass | 90 | 80 | 20 | 90 | 60 | 20 | 100 | 80 | 50 | 80 | 40 | 40 | 0 |
| Barnyardgrass | 90 | 30 | 0 | 90 | 40 | 0 | 0 | 0 | 0 | 70 | 20 | 0 | 0 |
| Nutsedge | 80 | 50 | 20 | 0 | 0 | 0 | 30 | 0 | 0 | 0 | 0 | 0 | 0 |
| Giant Foxtail | 80 | 20 | 0 | 60 | 20 | 0 | 0 | 0 | 0 | 60 | 0 | 0 | 0 |
| Wild Oats | 90 | 50 | 0 | 60 | 0 | 0 | 0 | 0 | 0 | 0 | 0 | 0 | 0 |
| Cocklebur | 80 | 40 | 0 | 90 | 30 | 0 | 70 | 0 | 0 | 0 | 0 | 30 | 0 |
| Morningglory | 90 | 70 | 40 | 90 | 80 | 0 | 90 | 80 | 70 | 80 | 40 | 60 | 30 |
| Teaweed | 80 | 50 | 0 | 0 | 0 | 0 | 70 | 30 | 0 | 0 | 0 | 20 | 0 |
| Sicklepod | 80 | 60 | 0 | 0 | 0 | 0 | 60 | 20 | 0 | 0 | 0 | 30 | 0 |
| Jimsonweed | 90 | 80 | 60 | 80 | 60 | 40 | 90 | 70 | 40 | 70 | 30 | 80 | 60 |
| Velvetleaf | 90 | 90 | 60 | 90 | 70 | 30 | 100 | 90 | 50 | 60 | 20 | 80 | 50 |
| PREEMERGENCE | | | | | | | | | | | | | |
| Rate g/ha | 250 | 62 | 16 | 4 | 250 | 62 | 16 | 250 | 62 | 16 | 250 | 62 | 250 | 62 |
| Corn | 100 | 80 | 30 | 0 | 90 | 70 | 20 | 90 | 80 | 20 | 30 | 0 | 50 | 20 |
| Wheat | 40 | 20 | 0 | 0 | 40 | 0 | 0 | 0 | 0 | 0 | 50 | 0 | 0 | 0 |
| Rice | 100 | 100 | 90 | 70 | 100 | 90 | 70 | 100 | 100 | 60 | 80 | 70 | 70 | 50 |
| Soybean | 90 | 80 | 30 | 0 | 50 | 30 | 0 | 90 | 80 | 20 | 40 | 0 | 60 | 20 |
| Cotton | 90 | 70 | 20 | 0 | 40 | 0 | 0 | 0 | 0 | 0 | 0 | 0 | 0 | 0 |
| Sugar beet | 100 | 80 | 60 | 20 | 90 | 70 | 20 | 100 | 90 | 30 | 60 | 0 | 80 | 30 |
| Rape | 90 | 50 | 20 | 0 | 0 | 0 | 0 | 80 | 20 | 0 | 0 | 0 | 0 | 0 |
| Crabgrass | 70 | 60 | 20 | 0 | 60 | 20 | 0 | 40 | 0 | 0 | 70 | 0 | 20 | 0 |
| Johnsongrass | 90 | 90 | 80 | 20 | 90 | 90 | 50 | 90 | 90 | 60 | 90 | 70 | 30 | 0 |
| Blackgrass | 100 | 100 | 90 | 80 | 100 | 80 | 50 | 100 | 90 | 80 | 90 | 80 | 70 | 50 |
| Barnyardgrass | 90 | 80 | 50 | 0 | 70 | 40 | 0 | 60 | 30 | 0 | 90 | 40 | 70 | 0 |
| Nutsedge | 90 | 90 | 50 | 0 | 60 | 20 | 0 | 90 | 30 | 0 | 0 | 0 | 30 | 0 |
| Giant Foxtail | 100 | 90 | 80 | 20 | 90 | 70 | 20 | 90 | 60 | 0 | 90 | 70 | 60 | 0 |

TABLE B-continued

| | Wild Oats | Cocklebur | Morningglory | Teaweed | Sicklepod | Jimsonweed | Velvetleaf |
|---|---|---|---|---|---|---|---|
| | 100 90 50 20 80 40 0 70 20 0 70 50 50 0 | 80 50 0 0 0 0 0 0 0 0 20 0 0 0 | 90 80 40 0 50 30 0 90 70 20 30 0 60 20 | 90 90 60 0 70 30 0 90 70 20 40 0 30 0 | 80 60 20 0 40 0 0 70 20 0· 0 0 20 0 | 100 90 70 0 80 30 0 90 70 20 20 0 40 0 | 90 90 60 20 90 20 0 90 80 30 20 0 80 20 |

(Previous rows continued from Table B)

| | Compound 6 | | | Compound 7 | | | | Compound 8 | | | Compound 9 | | | | Compound 10 | | | |
|---|---|---|---|---|---|---|---|---|---|---|---|---|---|---|---|---|---|---|
| POSTEMERGENCE | | | | | | | | | | | | | | | | | | |
| Rate g/ha | 62 | 16 | 4 | 62 | 16 | 4 | 1 | 62 | 16 | 4 | 62 | 16 | 4 | 1 | 62 | 16 | 4 | 1 |
| Corn | 90 | 80 | 50 | 0 | 0 | 0 | 0 | 40 | 20 | 0 | 70 | 50 | 0 | 0 | 70 | 20 | 0 | 0 |
| Wheat | 0 | 0 | 0 | 0 | 0 | 0 | 0 | 0 | 0 | 0 | 0 | 0 | 0 | 0 | 0 | 0 | 0 | 0 |
| Rice | 90 | 80 | 50 | 20 | 0 | 0 | 0 | 30 | 0 | 0 | 90 | 80 | 30 | 0 | 100 | 100 | 80 | 50 |
| Soybean | 90 | 90 | 80 | 0 | 0 | 0 | 0 | 80 | 30 | 0 | 90 | 90 | 80 | 30 | 100 | 100 | 90 | 60 |
| Cotton | 80 | 60 | 20 | 50 | 30 | 0 | 0 | 20 | 0 | 0 | 70 | 40 | 20 | 0 | 80 | 50 | 20 | 0 |
| Sugar beet | 100 | 90 | 80 | 100 | 100 | 90 | 50 | 100 | 90 | 50 | 100 | 95 | 90 | 50 | 100 | 100 | 90 | 50 |
| Rape | 0 | 0 | 0 | 0 | 0 | 0 | 0 | 0 | 0 | 0 | 20 | 0 | 0 | 0 | 20 | 0 | 0 | 0 |
| Crabgrass | 0 | 0 | 0 | 0 | 0 | 0 | 0 | 50 | 20 | 0 | 50 | 0 | 0 | 0 | 0 | 0 | 0 | 0 |
| Johnsongrass | 70 | 60 | 20 | 0 | 0 | 0 | 0 | 0 | 0 | 0 | 20 | 0 | 0 | 0 | 0 | 0 | 0 | 0 |
| Blackgrass | 40 | 20 | 0 | 40 | 0 | 0 | 0 | 0 | 0 | 0 | 80 | 50 | 20 | 0 | 90 | 70 | 60 | 20 |
| Barnyardgrass | 80 | 60 | 20 | 0 | 0 | 0 | 0 | 0 | 0 | 0 | 60 | 20 | 0 | 0 | 0 | 0 | 0 | 0 |
| Nutsedge | 0 | 0 | 0 | 20 | 0 | 0 | 0 | 30 | 0 | 0 | 20 | 0 | 0 | 0 | 40 | 30 | 0 | 0 |
| Giant Foxtail | 80 | 50 | 0 | 0 | 0 | 0 | 0 | 0 | 0 | 0 | 50 | 20 | 0 | 0 | 0 | 0 | 0 | 0 |
| Wild Oats | 20 | 0 | 0 | 0 | 0 | 0 | 0 | 0 | 0 | 0 | 20 | 0 | 0 | 0 | 0 | 0 | 0 | 0 |
| Cocklebur | 80 | 60 | 0 | 90 | 30 | 0 | 0 | 0 | 0 | 0 | 80 | 70 | 30 | 0 | 100 | 100 | 50 | 0 |
| Morningglory | 80 | 30 | 0 | 40 | 0 | 0 | 0 | 0 | 0 | 0 | 90 | 90 | 30 | 0 | 95 | 90 | 30 | 0 |
| Teaweed | 40 | 0 | 0 | 30 | 0 | 0 | 0 | 20 | 0 | 0 | 40 | 30 | 0 | 0 | 50 | 30 | 20 | 0 |
| SicklePod | 40 | 20 | 0 | 0 | 0 | 0 | 0 | 0 | 0 | 0 | 40 | 0 | 0 | 0 | 50 | 40 | 20 | 0 |
| Jimsonweed | 80 | 70 | 30 | 60 | 20 | 0 | 0 | 30 | 0 | 0 | 30 | 0 | 0 | 0 | 90 | 80 | 40 | 30 |
| Velvetleaf | 90 | 80 | 70 | 100 | 40 | 20 | 0 | 20 | 0 | 0 | 80 | 40 | 0 | 0 | 95 | 70 | 20 | 0 |
| PREEMERGENCE | | | | | | | | | | | | | | | | | | |
| Rate g/ha | 250 | 62 | 16 | 250 | | 62 | | 250 | | 62 | 250 | 62 | | 16 | 250 | 62 | | 16 |
| Corn | 90 | 50 | 20 | 0 | | 0 | | 0 | | 0 | 90 | 50 | | 20 | 80 | 20 | | 0 |
| Wheat | 20 | 0 | 0 | 0 | | 0 | | 0 | | 0 | 40 | 0 | | 0 | 0 | 0 | | 0 |
| Rice | 100 | 80 | 50 | 60 | | 0 | | 20 | | 0 | 90 | 80 | | 30 | 100 | 90 | | 40 |
| Soybean | 80 | 50 | 20 | 0 | | 0 | | 0 | | 0 | 80 | 40 | | 0 | 90 | 40 | | 0 |
| Cotton | 80 | 50 | 20 | 20 | | 0 | | 0 | | 0 | 70 | 40 | | 20 | 60 | 0 | | 0 |
| Sugar beet | 90 | 80 | 30 | 90 | | 20 | | 30 | | 0 | 90 | 80 | | 20 | 90 | 0 | | 30 |
| Rape | 0 | 0 | 0 | 0 | | 0 | | 0 | | 0 | 40 | 20 | | 0 | 60 | 30 | | 0 |
| Crabgrass | 50 | 30 | 0 | 0 | | 0 | | 20 | | 0 | 70 | 20 | | 0 | 90 | 60 | | 20 |
| Johnsongrass | 90 | 80 | 50 | 70 | | 0 | | 30 | | 0 | 70 | 50 | | 0 | 90 | 40 | | 0 |
| Blackgrass | 90 | 70 | 40 | 70 | | 40 | | 80 | | 40 | 90 | 80 | | 50 | 100 | 80 | | 80 |
| Barnyardgrass | 90 | 70 | 40 | 0 | | 0 | | 30 | | 0 | 90 | 60 | | 0 | 80 | 30 | | 0 |
| Nutsedge | 30 | 0 | 0 | 0 | | 0 | | 0 | | 0 | 0 | 0 | | 0 | 90 | 30 | | 0 |
| Giant Foxtail | 100 | 70 | 30 | 60 | | 0 | | 30 | | 0 | 90 | 70 | | 0 | 70 | 20 | | 0 |
| Wild Oats | 90 | 50 | 0 | 0 | | 0 | | 0 | | 0 | 80 | 60 | | 20 | 80 | 40 | | 0 |
| Cocklebur | 80 | 20 | 0 | 20 | | 0 | | 0 | | 0 | 70 | 40 | | 0 | 90 | 40 | | 0 |
| Morningglory | 80 | 40 | 0 | 70 | | 0 | | 0 | | 0 | 90 | 80 | | 30 | 90 | 50 | | 20 |
| Teaweed | 90 | 60 | 20 | 50 | | 0 | | 30 | | 0 | 80 | 60 | | 20 | 80 | 20 | | 0 |
| Sicklepod | 60 | 30 | 0 | 20 | | 0 | | 20 | | 0 | 60 | 30 | | 0 | 80 | 50 | | 0 |
| JimsonWeed | 90 | 40 | 0 | 40 | | 20 | | 20 | | 0 | 70 | 30 | | 0 | 90 | 60 | | 0 |
| Velvetleaf | 90 | 80 | 30 | 60 | | 0 | | 0 | | 0 | 70 | 40 | | 20 | 90 | 70 | | 30 |

What is claimed is:

1. A compound of the formula:

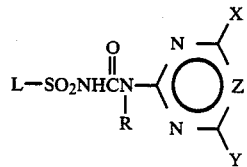

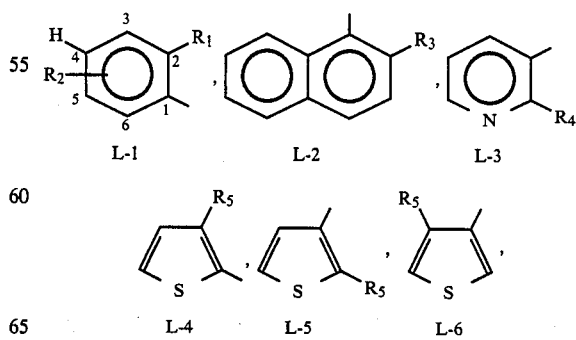

wherein

R is H or CH$_3$;

L is

-continued

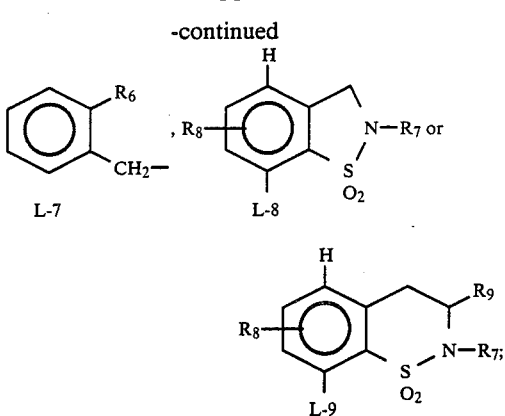

L-7    L-8

L-9

$R_1$ is F, Cl, Br, $NO_2$, $CO_2R_{10}$, $SO_2NR_{11}R_{12}$, $SO_2N(OCH_3)CH_3$, $CH_2OCH_3$, $CH_2OC_2H_5$ or Q;

Q is

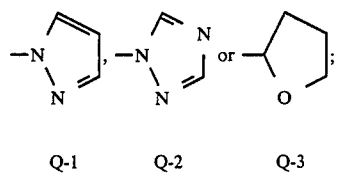

Q-1    Q-2    Q-3

$R_2$ is H, F, Cl, Br, $CF_3$, $CH_3$, $C_2H_5$, $OCH_3$, $OC_2H_5$, $SCH_3$ or $SC_2H_5$;

$R_3$ is H, $CH_3$, $OCH_3$, F, Cl, Br, $SO_2N(CH_3)_2$, $OSO_2CH_3$ or $S(O)_nCH_3$;

$R_4$ is $CH_3$, $C_2H_5$, $OCH_3$, $OC_2H_5$, F, Cl, Br, $SO_2NR_{11}R_{12}$, $SO_2N(OCH_3)CH_3$ or $S(O)_nR_{13}$;

$R_5$ is $C_1$-$C_3$ alkyl, F, Cl, Br, $NO_2$, $CO_2R_{10}$, $SO_2NR_{11}R_{12}$, $SO_2N(OCH_3)CH_3$ or $S(O)_nR_{13}$;

$R_6$ is $CO_2CH_3$, $CO_2C_2H_5$, $SO_2N(CH_3)_2$, $OSO_2CH_3$, $SO_2CH_3$ or $SO_2CH_2CH_3$;

$R_7$ is H, $C_1$-$C_5$ alkyl, $CH_2CH_2F$, $CH_2CH_2CH_2F$, $C_3$-$C_4$ alkenyl, $C_3$-$C_4$ alkynyl, $CH_3OCH_2CH_2$ or $C_2H_5OCH_2CH_2$;

$R_8$ is H, Cl, $CH_3$ or $OCH_3$;

$R_9$ is H or $CH_3$;

$R_{10}$ is $C_1$-$C_4$ alkyl, $CH_2CH_2OCH_3$, $CH_2CH_2Cl$, $CH_2CH=CH_2$ or $CH_2C\equiv CH$;

$R_{11}$ is H or $C_1$-$C_2$ alkyl;

$R_{12}$ is $C_1$-$C_2$ alkyl;

$R_{13}$ is $C_1$-$C_3$ alkyl;

n is 0, 1 or 2;

X is $NR_{14}R_{15}$;

$R_{14}$ is H or $C_1$-$C_2$ alkyl;

$R_{15}$ is $C_1$-$C_2$ alkyl, $OCH_3$, $OC_2H_5$ or $CH_2CN$;

Y is $OCH_2CH_2F$, $OCH_2CHF_2$ or $OCH_2CF_3$; and

Z is N;

and their agriculturally suitable salts.

2. Compounds of claim 1 wherein L is L-1, L-8 or L-9; and R is H.

3. Compounds of claim 2 wherein $R_1$ is $C_1$-$C_3$ alkyl, $C_1$-$C_3$ alkoxy, Cl, $NO_2$, $CO_2C_1$-$C_3$ alkyl, $SO_2N(CH_3)_2$, $SO_2CH_3$ or $SO_2C_2H_5$; $R_{14}$ is H; Z is N; and $R_2$ is in the 5-position of the phenyl ring.

4. Compounds of claim 3 wherein L is L-1 or L-8; and $R_7$ is H, $CH_3$ or $C_2H_5$.

5. Compounds of claim 4 wherein $R_{15}$ is $CH_3$; and $R_2$ is H.

6. The compound of claim 1 which is 2-[[[4-(methylamino)-6-(2,2,2-trifluoroethoxy)-1,3,5-triazin-2-yl]aminocarbonyl]aminosulfonyl]benzoic acid, methyl ester.

7. The compound of claim 1 which is 2-[[[4-(methylamino)-6-(2,2,2-trifluoroethoxy)-1,3,5-triazin-2-yl]aminocarbonyl]aminosulfonyl]benzoic acid, ethyl ester.

8. A composition suitable for controlling the growth of undesired vegetation which comprises an effective amount of a compound of claim 1 and at least one of the following: surfactant, solid or liquid diluent.

9. A composition suitable for controlling the growth of undesired vegetation which comprises an effective amount of a compound of claim 2 and at least one of the following: surfactant, solid or liquid diluent.

10. A composition suitable for controlling the growth of undesired vegetation which comprises an effective amount of a compound of claim 3 and at least one of the following: surfactant, solid or liquid diluent.

11. A composition suitable for controlling the growth of undesired vegetation which comprises an effective amount of a compound of claim 4 and at least one of the following: surfactant, solid or liquid diluent.

12. A composition suitable for controlling the growth of undesired vegetation which comprises an effective amount of a compound of claim 5 and at least one of the following: surfactant, solid or liquid diluent.

13. A composition suitable for controlling the growth of undesired vegetation which comprises an effective amount of the compound of claim 6 and at least one of the following: surfactant, solid or liquid diluent.

14. A composition suitable for controlling the growth of undesired vegetation which comprises an effective amount of the compound of claim 7 and at least one of the following: surfactant, solid or liquid diluent.

15. A method for controlling the growth of undesired vegetation which comprises applying to the locus to be protected an effective amount of a compound of claim 1.

16. A method for controlling the growth of undesired vegetation which comprises applying to the locus to be protected an effective amount of a compound of claim 2.

17. A method for controlling the growth of undesired vegetation which comprises applying to the locus to be protected an effective amount of a compound of claim 3.

18. A method for controlling the growth of undesired vegetation which comprises applying to the locus to be protectd an effective amount of a compound of claim 4.

19. A method for controlling the growth of undesired vegetation which comprises applying to the locus to be protected an effective amount of a compound of claim 5.

20. A method for controlling the growth of undesired vegetation which comprises applying to the locus to be protected an effective amount of the compound of claim 6.

21. A method for controlling the growth of undesired vegetation which comprises applying to the locus to be protected an effective amount of the compound of claim 7.

* * * * *